United States Patent
BEn-Yishai

(10) Patent No.: US 11,490,986 B2
(45) Date of Patent: Nov. 8, 2022

(54) SYSTEM AND METHOD FOR IMPROVED ELECTRONIC ASSISTED MEDICAL PROCEDURES

(71) Applicant: BEYEONICS SURGICAL LTD., Haifa (IL)

(72) Inventor: Rani BEn-Yishai, Haifa (IL)

(73) Assignee: BEYEONICS SURGICAL LTD., Haifa (IL)

( * ) Notice: Subject to any disclaimer, the term of this patent is extended or adjusted under 35 U.S.C. 154(b) by 0 days.

(21) Appl. No.: 17/483,838

(22) Filed: Sep. 24, 2021

(65) Prior Publication Data
US 2022/0008143 A1    Jan. 13, 2022

Related U.S. Application Data

(63) Continuation of application No. PCT/IL2020/051090, filed on Oct. 11, 2020.
(Continued)

(51) Int. Cl.
*A61B 90/00* (2016.01)
*G06T 7/73* (2017.01)
(Continued)

(52) U.S. Cl.
CPC .............. *A61B 90/37* (2016.02); *A61B 3/14* (2013.01); *A61B 34/20* (2016.02); *A61B 34/25* (2016.02);
(Continued)

(58) Field of Classification Search
None
See application file for complete search history.

(56) References Cited

U.S. PATENT DOCUMENTS 6,702,806 B2    3/2004  Gray et al.
6,837,892 B2 *  1/2005  Shoham ................. A61B 34/72
                                                606/130
(Continued)

FOREIGN PATENT DOCUMENTS

AU    2016405856    9/2018
CN    103903249    7/2014
(Continued)

OTHER PUBLICATIONS

Machine Translation: CN 110032936 A (Year: 2013).*
International Search Report dated Jan. 10, 2021 for corresponding Application No. PCT/IL2020/051090.

*Primary Examiner* — Michelle M Entezari
(74) *Attorney, Agent, or Firm* — Pearl Cohen Zedek Latzer Baratz LLP

(57) ABSTRACT

Methods and systems for displaying an image of a medical procedure (e.g., an intraoperative image) with additional information (e.g., data) that can augment the image of the medical procedure are provided. Augmenting the image can include overlaying data from a first image to a second image. Overlaying the data can involve determining, for a point or multiple points in the first image, a matching location or multiple matching locations in a second image. The first image and the second image can be of a patient. Determining the matching location can involve using a rotation and scale invariant geometrical relationship. The matching locations can be used as the basis for the overlay.

12 Claims, 14 Drawing Sheets

Related U.S. Application Data

(60) Provisional application No. 62/914,003, filed on Oct. 11, 2019.

(51) Int. Cl.

| | | |
|---|---|---|
| *G06T 3/40* | (2006.01) | |
| *G06T 3/60* | (2006.01) | |
| *A61B 34/20* | (2016.01) | |
| *A61B 34/00* | (2016.01) | |
| *G06V 10/44* | (2022.01) | |
| *A61B 3/14* | (2006.01) | |

(52) U.S. Cl.
CPC ............... *G06T 3/40* (2013.01); *G06T 3/602* (2013.01); *G06T 7/73* (2017.01); *G06V 10/443* (2022.01); *A61B 2034/2065* (2016.02); *G06T 2207/30041* (2013.01)

(56) References Cited

U.S. PATENT DOCUMENTS

| | | | |
|---|---|---|---|
| 6,866,661 B2 | 3/2005 | Gray et al. | |
| 6,929,638 B2 | 8/2005 | Gray et al. | |
| 7,784,947 B2 | 8/2010 | Perez et al. | |
| 7,905,887 B2 | 3/2011 | Moeller et al. | |
| 7,934,833 B2 | 5/2011 | Leblanc et al. | |
| 8,048,065 B2 | 11/2011 | Green et al. | |
| 8,414,123 B2 | 4/2013 | Boukhny et al. | |
| 8,486,085 B2 | 7/2013 | Moeller et al. | |
| 8,591,030 B2 | 11/2013 | Grecu et al. | |
| 8,708,488 B2 | 4/2014 | Kraus et al. | |
| 8,784,443 B2 | 7/2014 | Tripathi | |
| 9,149,340 B2 | 10/2015 | Boukhny et al. | |
| 9,173,717 B2 | 11/2015 | Tripathi | |
| 9,189,849 B2 | 11/2015 | Kersting et al. | |
| 9,226,798 B2 | 1/2016 | Tripathi et al. | |
| 9,295,380 B2 | 3/2016 | Kersting et al. | |
| 9,414,961 B2 | 8/2016 | Tripathi | |
| 9,462,944 B2 | 10/2016 | Moeller et al. | |
| 9,560,959 B1 | 2/2017 | Hopkins et al. | |
| 9,655,775 B2 | 5/2017 | Boukhny et al. | |
| 9,717,405 B2 | 8/2017 | Ren et al. | |
| 9,844,319 B2 | 12/2017 | Papac et al. | |
| 10,073,515 B2 | 9/2018 | Awdeh | |
| 10,117,721 B2 | 11/2018 | Tripathi et al. | |
| 10,213,104 B2 | 2/2019 | Grecu et al. | |
| 10,238,538 B2 | 3/2019 | Boukhny et al. | |
| 10,368,948 B2 | 8/2019 | Tripathi | |
| 10,398,300 B2* | 9/2019 | Levis | A61F 9/0017 |
| 10,460,457 B2 | 10/2019 | Heeren | |
| 2005/0119642 A1* | 6/2005 | Grecu | A61F 9/00804 606/5 |
| 2006/0094951 A1* | 5/2006 | Dean | G06T 17/10 600/407 |
| 2009/0177081 A1* | 7/2009 | Joskowicz | A61B 90/36 606/130 |
| 2010/0094262 A1 | 4/2010 | Tripathi et al. | |
| 2010/0177208 A1* | 7/2010 | Tamaru | H04N 5/2621 348/222.1 |
| 2011/0122365 A1 | 5/2011 | Kraus et al. | |
| 2014/0073907 A1* | 3/2014 | Kumar | A61B 10/0241 600/407 |
| 2015/0051725 A1* | 2/2015 | Lee | G16H 50/50 700/98 |
| 2015/0077528 A1* | 3/2015 | Awdeh | A61B 3/005 348/78 |
| 2016/0051360 A1 | 2/2016 | Tripathi et al. | |
| 2016/0113727 A1 | 4/2016 | Tripathi et al. | |
| 2016/0189002 A1* | 6/2016 | Kawakami | G06V 10/757 382/218 |
| 2016/0346047 A1 | 12/2016 | Tripathi et al. | |
| 2017/0189233 A1* | 7/2017 | Dewey | A61B 3/103 |
| 2017/0249737 A1 | 8/2017 | Piron et al. | |
| 2018/0008460 A1* | 1/2018 | Tanzer | A61B 3/12 |
| 2019/0069971 A1 | 3/2019 | Tripathi et al. | |
| 2019/0120619 A1* | 4/2019 | Miura | G01B 21/04 |
| 2019/0142359 A1* | 5/2019 | Zhang | A61B 34/20 606/130 |
| 2021/0074004 A1* | 3/2021 | Wang | G06T 7/73 |
| 2021/0074054 A1* | 3/2021 | Deng | G06T 11/00 |
| 2021/0192759 A1* | 6/2021 | Lang | A61B 34/10 |

FOREIGN PATENT DOCUMENTS

| | | |
|---|---|---|
| CN | 104766323 | 7/2015 |
| CN | 110032936 A * | 7/2019 |
| EP | 2634749 | 9/2013 |

* cited by examiner

SYSTEM AND METHOD FOR IMPROVED ELECTRONIC ASSISTED MEDICAL PROCEDURES

CROSS REFERENCE TO RELATED APPLICATIONS

This application is a continuation of PCT International Application No. PCT/IL2020/051090, International Filing Date Oct. 11, 2020, which claims the benefit of U.S. Provisional Patent Application No. 62/914,003, filed Oct. 11, 2019, both are incorporated herein by reference in their entireties.

FIELD OF THE INVENTION

The invention relates generally to the field of computer assisted surgeries. In particular, the invention relates to image guided surgeries.

BACKGROUND OF THE INVENTION

Currently, computing systems for assisted surgeries exist (e.g., image guided surgical systems). Some current systems include displays that can allow persons (e.g., medical professionals, surgeons, nurses, and/or other persons) to view medical data while a medical procedure (e.g., a surgery) is performed. In some systems, a desired location for an object with respect to the surgery can be displayed to a surgeon. In some systems, an object image can be superimposed on (e.g., overlaid with) an intraoperative image. For example, during intraocular lens (IOL) placement.

In the case of IOL placement, some types of IOLs can require that the IOL is positioned in a specific orientation and/or location within a patient's eye (e.g., toric IOLs, multifocal IOLs). In current systems, a desired orientation and/or location for the IOL with respect to a preoperative image of an eye (e.g., an image of an eye taken prior to the surgery) can be determined by, for example, various current diagnostic devices. The preoperative image can be captured by the diagnostic device concurrently with sampling the data that is used for calculating the desired IOL positioning (orientation and/or location).

Typically, the position/condition of an eye during preoperative imaging is at least slightly different form the position/condition of the same eye during the surgery. For example, a patient may be sitting when the pre-operative image is taken vs. lying down during the surgery. In another example, the eye may have drops and/or tools inserted during the surgery that are not present during the preoperative imaging.

Differences in the position/condition of the eye at the time preoperative imaging is done versus the time surgery is performed can cause differences between information in the imaging obtained in a preoperative imaging stage and information obtained during imaging during the surgery (e.g., the intraoperative imaging).

Some current systems can generate a list of feature pairs, one in each of the preoperative image and the intraoperative image, that are assumed to be identical, and use these feature pairs to calculate a global mapping from preoperative image to the intraoperative image. In mapping the pre-operative image onto the intraoperative image, some prior systems use shifts and/or rotations, and find a best fit. Current systems that typically track and/or lock on images can also typically require an orientation calculation, a shift calculation, and/or an image correlation calculation also calculating a best fit, e.g., a single mathematical function to best fit. However, there can be distortions in the images due to, for example, liquid inserted into the eye and on the eye, tubes in the eye, tools touching the eye, differences between imaging systems for the pre-operative image and the real-time image, which can cause a best fit to be erroneous.

While current systems may account for some difficulties during surgery, accuracy of the information presented, ease of use of the information presented, and/or timing of the information presented can be improved. Therefore, it can be desirable to improve electronically assisted surgical systems.

SUMMARY OF THE INVENTION

In one aspect, the invention involves a method for determining, for a point in a first image, a matching location in a second image, the first image and the second image are of a patient. The method involves (a) receiving, via a computing device, the point having a location in the first image, (b) receiving, via the computing device, two feature pairs wherein each feature pair comprises one feature location from the first image and a matching feature location from the second image, (c) determining, via the computing device, a first triangle with respect to the first image, such that the vertexes of the first triangle are the locations of the two features of the two feature pairs that are from the first image and the location of the point in the first image, (d) determining, via the computing device, a second triangle with respect to the second image, such that two of the vertexes of the second triangle are the locations of each of the respective matching features of the two feature pairs that are from the second image, and such that the second triangle has triangle similarity with the first triangle, yielding a location of a third vertex, and (e) determining, via the computing device, the matching location in the second image of the point in the first image based on the location of the third vertex, wherein the first image and the second image are selected from at least one of a preoperative image and an intraoperative image of the patient.

In some embodiments, the two feature pairs are selected from a set of feature pairs. In some embodiments, the two feature pairs are selected based on distance of the two features of the two feature pairs that are from the first image to the point. In some embodiments, an order of the vertices in the second triangle proceeding clockwise is the same as the order of the respective matching vertices in the first triangle proceeding clockwise.

In some embodiments, each vertex angle in the second triangle is equal to the vertex angle of its respective matching vertex in the first triangle. In some embodiments, the images of the patient are images of an eye of the patient. In some embodiments, the images are of an exterior eye and the feature locations are in the limbus area of the eye in the images. In some embodiments, the images are of the retina of the eye.

In some embodiments, the method involves repeating the method of claim 1 for each of multiple points, wherein the multiple points are generated from guidance information that is to be overlaid on the second image and wherein the two feature pairs are updated for each of the multiple points.

In some embodiments, the method involves repeating steps (b) through (d) for each of a plurality of feature pairs to determine a plurality of corresponding third vertex locations, calculating an averaged third vertex location, ad determining the matching location in the second image of the point in the first image based on the averaged third vertex location.

In some embodiments, the method also involves in step (e), setting the location of the third vertex as the matching location in the second image of the point in the first image. In some embodiments, the method also involves setting the averaged third vertex location as the matching location in the second image of the point in the first image.

In another aspect, the invention involves a method for determining, for a point in a first image, a matching location in a second image, the first image and the second image are of a patient. The method involves receiving, via a computing device, the point having a location in the first image. The method also involves receiving, via the computing device, at least two feature pairs wherein each feature pair comprises one feature location from the first image and a matching feature location from the second image, wherein each of the features in each feature pair has a corresponding location in its respective image. The method also involves determining, via the computing device, a geometrical relationship with respect to the first image, based on the locations of the at least two features pairs and the location of the point in the first image, wherein the geometrical relationship is scale and rotation invariant. The method also involves determining, via the computing device, the matching location in the second image based on the geometrical relationship and the locations of the respective matching features of the at least two feature pairs that are from the second image. wherein the first image and the second image are selected from at least one of: a preoperative image and an intraoperative image of the patient.

In another aspect, the invention involves a method for filtering a set of feature pairs between two images, the two images are of a patient. The method involves receiving, by a computing device, a set of feature pairs wherein each feature pair comprises one feature location from a first image and a matching feature location from a second image. The method also involves filtering, by the computing device, the set of feature pairs based on at least one of a scale invariant and a rotational invariant geometrical relationship between feature locations from the set of feature pairs, wherein the two images are selected from at least one of: a preoperative image and an intraoperative image of the patient.

In some embodiments, the filtered set of feature pairs has less feature pairs then the received set of feature pairs. In some embodiments, filtering the received set of feature pairs reduces false feature pairs in the set of feature pairs.

In some embodiments, the filtering also involves determining, by the computing device, a set of couples of features, determining, by the computing device, for each couple of the set of couples a first distance between the two feature locations of the two feature pairs of the couple that are from the first image, determining, by the computing device, for each couple of the set of couples a second distance between the two feature locations of the two feature pairs of the couple that are from the second image, determining, by the computing device, for each couple of the set of couples a ratio between the first distance and the second distance, yielding a set of respective ratios, and discarding feature pairs based on the set of respective In some embodiments, the method involves determining, by the computing device, a relative scale between the two images, based on the set of respective ratios, and determining, by the computing device, a selected feature pair to be discarded from the set of feature pairs based on the determined relative scale and based on the ratios that were determined using the selected feature pair.

In some embodiments, the filtering involve determining, by the computing device, a set of couples of feature pairs, determining, by the computing device, for each couple of the set of couples a first angle of a line connecting the two feature locations of the two feature pairs of the couple that are from the first image, determining, by the computing device, for each couple of the set of couples a second angle of a line connecting the two feature locations of the two feature pairs of the couple that are from the second image, determining, by the computing device, for each couple of the set of couples a difference of angles between the first angle and the second angle, yielding a set of respective differences of angles, and discarding feature pairs based on said set of respective differences of angles.

In some embodiments, the discarding involves determining, by the computing device, a rotation between the two images, based on the set of respective differences of angles, and determining, by the computing device, a selected feature pair to be discarded from the set of feature pairs based on the determined rotation and based on the differences of angles that were determined using the selected feature pair.

In some embodiments, the filtering involves selecting at least three feature pairs from the set of feature pairs, determining, via the computing device, a first polygon with respect to the first image, such that the vertexes of the first polygon are the feature locations of the at least three feature pairs that are from the first image, determining, via the computing device, a second polygon with respect to the second image, such that the vertexes of the second polygon are the feature locations of the at least three feature pairs that are from the second image, determining via the computing device, whether the first and second polygons are similar and when the two polygons are not similar, discarding from the set of feature pairs at least one feature pair of the at least three feature pairs.

BRIEF DESCRIPTION OF THE DRAWINGS

Non-limiting examples of embodiments of the disclosure are described below with reference to figures attached hereto that are listed following this paragraph. Dimensions of features shown in the figures are chosen for convenience and clarity of presentation and are not necessarily shown to scale.

The subject matter regarded as the invention is particularly pointed out and distinctly claimed in the concluding portion of the specification. The invention, however, both as to organization and method of operation, together with objects, features and advantages thereof, can be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

DETAILED DESCRIPTION

Figure 1:
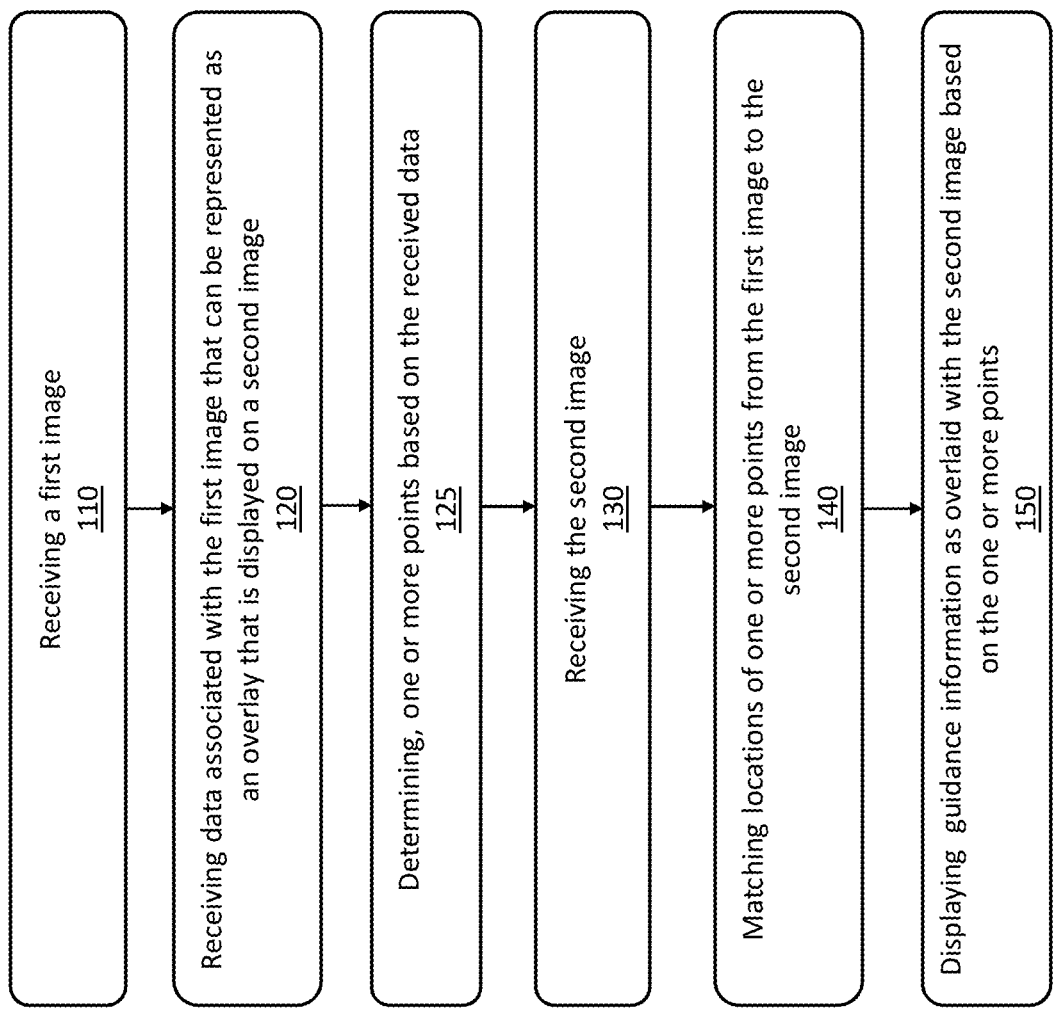
FIG. 1 is a flow chart showing a method for locating data from a first image on a second image, according to some embodiments of the invention.

In the following detailed description, numerous specific details are set forth in order to provide a thorough understanding of the invention. However, it will be understood by those skilled in the art that the invention can be practiced without these specific details. In other instances, well-known methods, procedures, and components, modules, units and/ or circuits have not been described in detail so as not to obscure the invention.

Generally, the invention can involve displaying an image of a medical procedure (e.g., an intraoperative image) with additional information (e.g., data) that can augment the image of the medical procedure. The data can be overlay data. The overlay data can be shapes, information e.g., guidance information), or any visual output that is desired to be displayed concurrent with or appear on top of the intraoperative image. The overlay data can be images that appear to be positioned on top of the intraoperative image. The overlay data can be displayed such that it varies in color, intensity, opacity, transparency, or any combination thereof.

Each pixel on the image to be displayed during the medical procedure can be assigned a value. The value for each pixel can depend on the intraoperative image and the overlay data. The overlay data can cause the pixels in the intraoperative image to be modified, according to the desired image output for the medical procedure.

Overlaying data with an image (e.g., a preoperative image or an intraoperative image) can assist a medical professional during a medical procedure. For example, during ophthalmic surgery it can be desirable for a surgeon to understand where surgical incisions or treatments are planned to take place, and/or where medical objects are planned to be placed, such as for example for capsulotomy, limbal relaxing incisions (LRIs), stitches, retinal laser photocoagulation, and/or IOL insertion. The planning information can be presented to the surgeon as overlay data on the intraoperative image. For example, when inserting a toric IOL into an eye, the correct orientation of the IOL can be imperative to the patient's ability to see properly after the surgery. Toric IOLs typically include markers (e.g., axis marks) that can help a surgeon align the IOL within the patient's eye properly. However, the IOL's markers can only assist in the IOL's placement within the patient's eye if there is an accurate, stable, and timely reference.

The invention can include methods and systems that can allow an accurate, stable and/or timely reference for IOL alignment. As is apparent to one of ordinary skill in the art, the method and systems discussed herein can be applicable to any electronic assisted surgery where an object (e.g., a tool, an implant and/or any medical object) is positioned at a predefined desired location and/or orientation on or within a patient, or where a surgical treatment (e.g. an incision, a biopsy, and/or a tumor ablation) is taken place at a pre-planned location.

In general, the invention can allow for i) overlaying preoperative guidance information (e.g., guidance data) with an intraoperative image, e.g., overlaying information from a pre-operative image, or information associated with a pre-operative image, with an intraoperative image that can be a live image or a still image taken at a particular moment in time of the real-time surgical procedure, ii) overlaying an indicator of a current location and/or orientation of a medical object during the medical procedure with a preoperative image, e.g. a preoperative image as taken by a diagnostic device, or a preoperative image already overlaid with pre-planning or guidance information, and iii) overlaying intraoperative guidance information with an intraoperative image, e.g. overlaying information associated with a live image viewed by one surgeon with a live image viewed by another surgeon, or overlaying information associated with a still image taken at a particular moment during the surgical procedure with a live image.

As an example, for overlaying preoperative guidance information with a live image (e.g., an intraoperative image), a surgeon may view a guidance information overlay indicating a preplanned location and/or orientation of an IOL overlaid with the live image while moving and/or rotating the IOL. As an example, for overlaying intraoperative guidance information with the live image, a supervising surgeon may draw a line indicating a desired location for an incision on an intraoperative image (e.g. a snapshot of the live image), and a resident performing the procedure may view the line overlaid with the live image. As an example for overlaying guidance information with a preoperative image, a surgeon may view the preoperative image overlaid with guidance information concurrently with viewing the live image (e.g. in a picture-in-picture view or a side-by-side view).

In the latter example, two indicators (e.g. two lines for indicating orientation and optionally also location, or two circles for indicating location) may be overlaid with the preoperative image. A first indicator may represent the desired location and/or orientation of an IOL, and can remain unchanged with respect to the preoperative image it is overlaid upon. However, a second indicator may represent the actual IOL location and/or orientation during the medical procedure, and can be continually updated (e.g., with a predefined periodic rate) as the surgeon manipulates the IOL. The surgeon can see in real-time an indicator representing the actual IOL location and/or orientation with respect to an indicator representing the desired IOL location and/or orientation, and can change the IOL location and/or orientation until the two symbols are in alignment the surgeon can concurrently see both the guidance overlay on the preoperative image, and the IOL in the live image).

In some embodiments, a surgeon may be concerned with only the IOL orientation and not the location. In these embodiments, for example when the two indicators (e.g. lines) are parallel to each other they can be considered to be in alignment. In some embodiments, a surgeon is concerned with only the location of the medical device. In these embodiments, for example, when the two indicators (e.g. circles) are concentric they can be considered to be in alignment. In some embodiments, a surgeon is concerned with both the location and the orientation. In various embodiments, the surgeon can decide when the two indicators have reached a sufficiently aligned state.

Generally, the methods and systems can allow for i) displaying with the intraoperative image indicators that are associated with locations in a preoperative image, ii) displaying with the preoperative image indicators that are associated with locations in the intraoperative image, and iii) displaying with one intraoperative image indicators that are associated with locations in another intraoperative image.

Accurately matching locating) a point in one image (e.g., a first image) on another image (e.g., a second image) can involve finding a most accurate location on the second image that corresponds to the point on the first image. Accurately matching a point in one image on another image can also be referred to as copying the point from one image to another image. Although the two images may be of the same object (e.g., two images are of the same patient's eye), the two images may not to be identical (e.g., the two images are of the same patient's eye taken at two different times). Thus, matching a point (e.g., a desired location for a center of an IOL) in a first image (e.g., preoperative image) to a point in a second image (e.g., a intraoperative image) can involve locating a point on the second image that closely corresponds to the point on the first image, as described in further detail below with respect to FIG. 1

In some embodiments, locating the correct point can involve finding a location relative to adjacent anatomical elements in both images that are identical. The anatomical elements of a reference can depend on the type of the surgical procedure and/or the stage of the procedure. For example, in open brain surgery, superficial cortical vasculature can serve as reliable anatomical elements for transfer of locations at the initial stages of the procedure, but once a tumor is partially removed they may be considered unreliable as the brain tissue is subject to deformation. In another example, in anterior ophthalmic procedures anatomical elements near the limbus may be considered reliable, and conjunctival blood vessels distant from the limbus may be considered unreliable. This can be due to possible movement of the conjunctiva relative to the sclera due to surgical manipulations.

Locations (e.g., one or more points) in each of the respective images can be transferred to the other images by determining corresponding locations in the other respective image. In some embodiments, corresponding locations can be determined based on aligning the two images. In some embodiments, corresponding locations can be determined as described in further detail in FIG. 1 below. A location can be an XY coordinate system location in the image, having sub-pixel resolution (e.g., non-integer x and y values). Each image can be defined as having pixels, pixel locations, and the pixel locations can be defined in an XY coordinate system. The location of points and/or objects within images can also be referred to in an XY coordinate system.

FIG. 1 is a flow chart showing a method 100 for locating data from a first image on a second image, according to some embodiments of the invention. The method can include receiving the first image (Step 110).

The first image (e.g., reference image) can be a preoperative image. The preoperative image can be an image of a patient taken prior to an operation. The first image can show a region of interest which can be a portion of patent that is of interest, for example, for a procedure. For example, an eye, a brain, a lung or a blood vessel.

The first image can be a two-dimensional (2D) image, for example in ophthalmic surgery an image of an eye generated by a CCD- or CMOS-based camera, or an image of a retina generated by an SLO camera. The 2D image can be generated from a three-dimensional (3D) imaging dataset, for example in brain surgery, an oblique slice generated from a CT imaging dataset, or a rendered image of a 3D segmented model of a tissue generated from an MRI imaging dataset, or for example in ophthalmic surgery an en-face image or a summed voxel projection image generated from an OCT imaging dataset.

The method can also include receiving data (e.g., overlay data) that is associated with the first image that can be represented as an overlay that is displayed on a second image (e.g., an intraoperative image) (Step 120). The overlay data can be guidance information for the medical procedure determined during the capturing of the preoperative image. The guidance information (e.g., reference data) can include a desired location and/or orientation for a medical object within the first image. The guidance information can be a desired location for insertion, placement and/or positioning of any kind of the medical object with respect to the patient. For example, the data can be xy coordinates of a center of a visual axis and an orientation, and it can be represented as a line centered and oriented per the data and is displayed as an overlay with the second image. The guidance information can be a desired location for a surgical treatment. For example, the data can be a contour (e.g., an arc or a line) of a planned incision, a location of a planned biopsy, and/or a location of a planned tumor ablation, that can be represented as overlays on the second image.

The guidance information can indicate a portion of an eye. The guidance information can indicate a particular object in the first image. The guidance information can have characteristics that can cause it to be displayed as a line, a dot, a series of dots, a color, or any visual indicator as is known in the art. In some embodiments, for an IOL placement, the guidance information can indicate an orientation relative to the image for IOL placement and/or the desired IOL placement location.

In some embodiments, the guidance information is received by the system. In some embodiments, the guidance information is automatically generated by a diagnostic device. In some embodiments, the guidance information is not automatically generated by a diagnostic device. In various embodiments, if the guidance information is not automatically generated by a diagnostic device (e.g., such as the toric IOL location and orientation data), or if a surgeon chooses to change automatically generated guidance information, the surgeon may use a SW tool (e.g. a dedicated SW tool) for overlaying or drawing on the preoperative image (or a first image) any of the following: circles, lines, other geometrical shapes, freehand drawing. The overlays can indicate areas by shapes filled, e.g. by texture or color. The SW tool may store the overlay as textual data that is used during a procedure to generate an overlay on the intraoperative image. For example, guidance information for a capsulotomy can be a circle having a known diameter drawn as an overlay with the preoperative image.

The method can also involve determining one or more points based on the received data (Step 125). The received data (e.g. guidance information) can be represented as a series of locations (e.g. points) in the first image coordinate system (CS). For example, a circle can be represented by 10 points uniformly spread along the circle. In these embodiments, during a procedure, the points can be located in the intraoperative image (e.g., a live image). Locating the points in the intraoperative image can involve, copying the points from a preoperative CS to an intraoperative CS. In some embodiments, once the points are copied to the intraoperative image CS, the method can involve reconstructing the guidance information based on the copied points. For example, calculating a circle that fits (e.g, best fits) the 10 copied locations. In these embodiments, the reconstructed guidance information can be displayed as an overlay with the intraoperative image.

In some embodiments, the received data is represented as points prior to the procedure. In some embodiments, the received data is represented as points prior during the procedure. For example, the circle that the surgeon draws on the preoperative image is guidance information that is associated with the preoperative image (e.g., and/or stored) as, for example, a center (x and y values) and radius (in pixels), and the points to be copied can be generated during a procedure that takes place after the surgeon draws on the preoperative image (e.g., generated in real-time during the surgery).

In some embodiments, limbal relaxing incisions (LRIs) are represented by guidance information showing short line segments or shorts arcs having a geometrical representation in the preoperative image CS, or as a series of points. In some embodiments, areas where a retina is detached are indicated on a preoperative image of a retina by a contour filled with a color.

In various embodiments, guidance information that is displayed as an overlay can be represented for instance as an OpenGL object (e.g. by a list of vertexes and textures) that can include a finite number of locations that may be copied from one image CS to another (e.g., a preoperative image to an intraoperative image). In various embodiments, the first image can be an intraoperative image (e.g., a live image) and the guidance information can be automatically generated by detecting IOL axis marks.

In various embodiments, the guidance information is automatically and/or manually generated, in association with either a preoperative image or an intraoperative image. In various embodiments, the guidance information is automatically generated with respect to a preoperative image (e.g. by a diagnostic device), manually generated with respect to a preoperative image (e.g. by a surgeon as described above), automatically generated with respect to an intraoperative image (e.g. by detecting or tracking a tool or an implant with respect to the live image), and/or manually generated with respect to an intraoperative image (e.g. by drawing a teaching symbol on an intraoperative snapshot).

In various embodiments, the first image is an intraoperative image. The intraoperative image can be a real-time image. The intraoperative image can be a live image or a still image. As is apparent to one of ordinary skill in the art, the live image can be a series of still images continuously changing in real-time.

In various embodiments, the second image is an intraoperative image.

In various embodiments, the first image is a still image (e.g., a snapshot) of the intraoperative image and the second image is a live image. In some embodiments, the guidance information can be a line drawn on the snapshot, for example, by a senior surgeon.

In various embodiments, the first image is a preoperative image. The preoperative image can be a still image or a video image. In various embodiments, the second image is a preoperative image.

In various embodiments, the first image is a preoperative image and the second image is an intraoperative image (e.g., a live image or snapshot). In these embodiments, the guidance information can be generated by a diagnostic device or by the surgeon, and can be represented as locations in the preoperative image CS The method can also include receiving the second image (Step 130). For example, the second image can be received during the medical procedure. The second image can be an intraoperative image (e.g., a live image of the medical procedure or snapshot of the medical procedure), a preoperative image and/or any image as described with respect step 120.

The method can also include, matching locations of one or more points from the first image to the second image (Step 140). The one or more points can be based on the received data, for example, as described above in Step 125. For example, the guidance information associated with the preoperative image can be represented by points (e.g., two points representing a line) in the preoperative image CS. The method can also involve displaying guidance information as overlaid with the second image based on the one or more points (Step 150).

In some embodiments, when the guidance information is an indicator that is overlaid on a live image, it is locked to anatomical elements of reference in the live image such that the guidance information moves when there is movement in the live image.

In some embodiments, when the guidance information is an indicator that is associated with a location of an object in the live image and it is overlaid on a preoperative image, the overlay can dynamically change when the object moves relative to anatomical elements of reference in the live image.

In some embodiments, multiple preoperative diagnostic tests are averaged to generate the guidance information. For example, in toric alignment guidance, when multiple astigmatism measurements are preoperatively performed by one or more devices, the various results are accurately averaged when, for instance, each measurement is accompanied with an image of the eye sampled concurrently with the diagnostic test. In various embodiments, the method involves selecting one of the multiple diagnostic images as a reference image (e.g., first image), and converting the various astigmatism measurements from the CS of each of the multiple diagnostic images to the CS of the reference image. This can be based on aligning each of the diagnostic images to the selected reference image and adjusting the corresponding astigmatism measurements according to the relative rotation between the images. In some embodiments, an astigmatism measurement can be represented as two points in the diagnostic image CS, and the location of these two points is copied to the reference image CS. In some embodiments, averaging multiple preoperative diagnostic tests to generate the reference data involves automatically discarding outlier results. In some embodiments, the user decides which results to include in the averaging.

Figure 2:
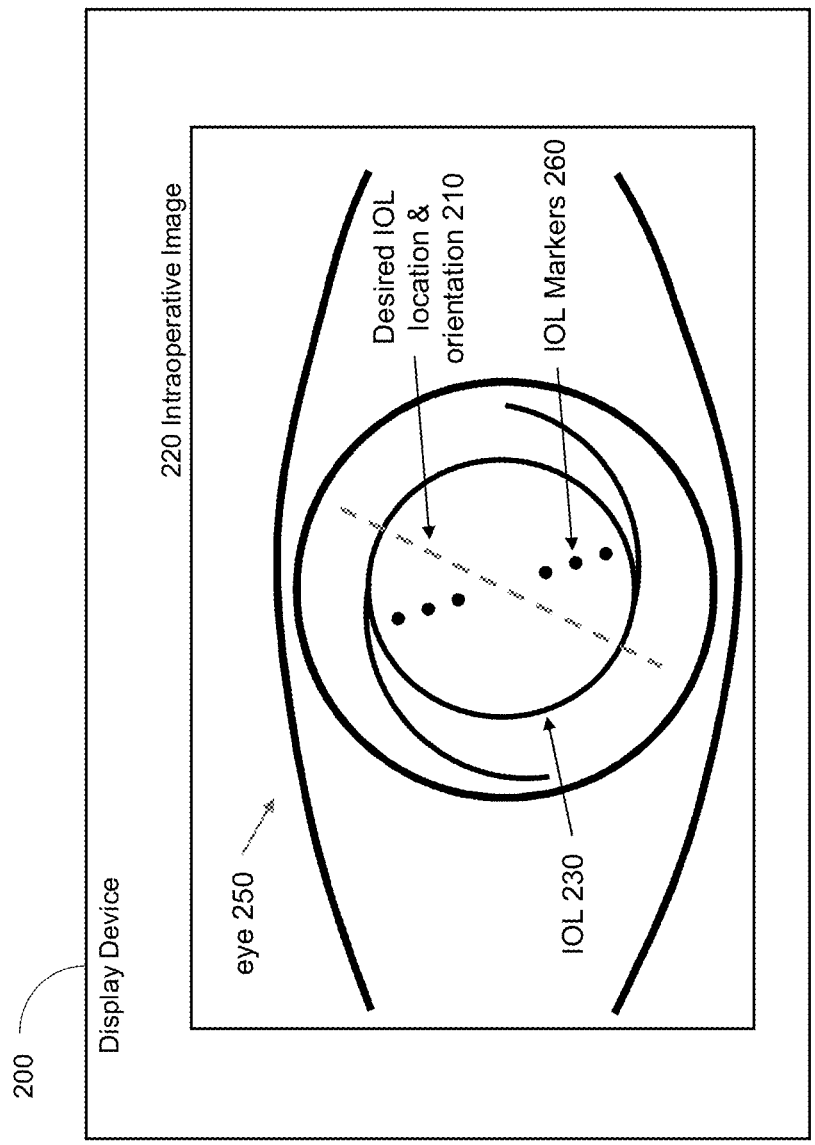
FIG. 2 is diagram showing an example of a display device displaying guidance information as an overlay superimposed on an intraoperative image, according to some embodiments of the invention.

Turning to FIG. 2, FIG. 2 is diagram showing an example of display device 200 displaying guidance information as an overlay in the form of a dashed line 210 (e.g., desired IOL location and orientation) superimposed on the intraoperative image 220 showing IOL 230 after being inserted to an eye 250, according to some embodiments of the invention. The current orientation of the IOL is apparent via IOL markers 260.

The toric IOL in FIG. 2 includes six dots (or markings) that can indicate a steep or flat axis of the toric IOL. Toric IOLs typically include axis marks, such as a series of dots, lines, rectangles and/or other markings as are known in the art, that can assist a surgeon to align the IOL to a predetermined orientation. These markings can be detected in an intraoperative image, e.g. by a template-matching algorithm, a deep-learning algorithm, and/or any algorithm known in the art to detect the markings. Once the locations of the IOL markings in the intraoperative image are known, the system can determine, for example, the location of the center of the IOL in the intraoperative image. The guidance information (e.g., overlay) can correspond to the optical axis that the axis marks indicate, e.g., an overlay for an IOL with indications for a steep axis that is orthogonal to an overlay for an IOL with indications for a flat axis (e.g., either the IOL type can be detected automatically or a user can indicate if the IOL type is different from a default type).

In various embodiments, for IOL insertion, the guidance information indicates a desired location and/or orientation of the IOL. In some embodiments, the guidance information is locked (e.g., pinned) to a desired location (e.g. relative to the eye). In some embodiments, for toric IOL insertion, the guidance information indicates the desired orientation of the IOL.

In some embodiments, for toric IOL insertion, the guidance information is displayed as an overlay centered on a center of the IOL as detected in the intraoperative image. In this manner, the indicator of the desired IOL orientation can be pinned (or locked) to the IOL center. For instance, the user may choose to pin the overlay to the IOL center once the IOL is at its final position, e.g., for fine tuning and/or for verifying the alignment. When a user chooses to pin the overlay to the IOL center, and the IOL center is temporarily not being detected (e.g. due to obscurations by the iris or by tools), the overlay can be centered on either one of the last determined IOL center location or the preoperatively determined (e.g., desired) IOL location.

In some embodiments, when the intended overlay location changes abruptly, the overlay is gradually shifted to the updated (e.g., intended) location. Abrupt changes in the intended overlay location can occur when a user changes the selection of overlay centering from pinning to the preplanned (e.g., desired) location to pinning to the IOL center, or vice versa, or when the overlay is chosen to be pinned to the IOL center but the IOL center is temporarily not detected.

Detecting the IOL center may be based, for example, on detecting the IOL contour or detecting the IOL axis marks. When the IOL shape is known, detecting the IOL center can be based on detecting segments of the IOL boundaries. For example, when the IOL is round (e.g., disregarding the haptics), segments of the IOL edges can be detected, and/or the center of a circle that best fits these segments can be determined as the IOL center. Detecting the axis marks locations may be determined for example based on the IOL type (e.g., a known IOL type has a known number of the axis marks and known distances between the axis marks). In another example, the axis mark locations may be determined based on estimating the most likely location based on a nominal IOL diameter and/or based on known patterns for various toric IOLs in the market.

In some embodiments, the angular difference between the desired IOL orientation and the current IOL orientation is determined. The angular difference can be conveyed to a user various visual and or auditory ways.

In some embodiments, the angular difference between a desired IOL orientation and the current IOL orientation can be determined, for example, by detecting the IOL axis marks in the intraoperative image, and copying the axis marks locations from the intraoperative image CS to the preoperative image CS. An angle of a line that best fits the copied locations in the preoperative image CS may be calculated, and the difference between this angle and the preplanned desired angle may be determined.

In various embodiments, the method can involve generating and/or reporting a confidence score that can control an appearance of the guidance overlay. For example, if a surgeon is causing rapid movement in an eye, the color of the guidance overlay can change to reflect that it may be less accurate during the rapid movement. The confidence score can also be conveyed to the user via a separate symbol (e.g., a colored and/or numbered meter).

In some embodiments, the system may use auditory indications to assist the surgeon, e.g. when the surgeon chooses not to see an overlay on a live image. For example, the system can be programmed to calculate the positional and/or angular difference (e.g., the measure of alignment) between a desired IOL location and/or orientation and a current IOL location and/or orientation. The measure of alignment can be determined without actually displaying the indicators that represent the desired IOL location and/or orientation and the current IOL location and/or orientation, and can be calculated based on their relative location and/or orientation. The calculations can be based on copying the locations of the detected axis marks from the intraoperative image CS to the preoperative image CS, and/or by copying the desired IOL location and/or orientation from the preoperative image CS to the intraoperative image CS. When the IOL does not have axis marks and the guidance information includes a desired location only, the IOL location can be detected in the live image for instance based on detecting its contour in the live image. Having calculated a measure (or score) of alignment, the system can generate an auditory indicator that indicates to the surgeon how close the actual IOL location and/or orientation is with respect to the desired IOL location and/or orientation. Such an indicator may be for instance a beeping sound having a frequency increasing with the alignment score.

In some embodiments, the surgeon relies on an auditory indicator alone. In some embodiments, once an alignment score threshold is met, a PIP can be presented to the surgeon automatically. In some embodiments, the PIP can appear when the surgeon presses a footswitch. In some embodiments, a surgeon momentarily freezes a live image to see the desired indicator overlaid with the intraoperative snapshot image, before returning to the live image to improve the alignment.

In some embodiments, known models of particular IOLs are used. In some embodiments for other medical procedures, models of known medical objects/devices can be used for detection in the intraoperative image.

Figure 3A:
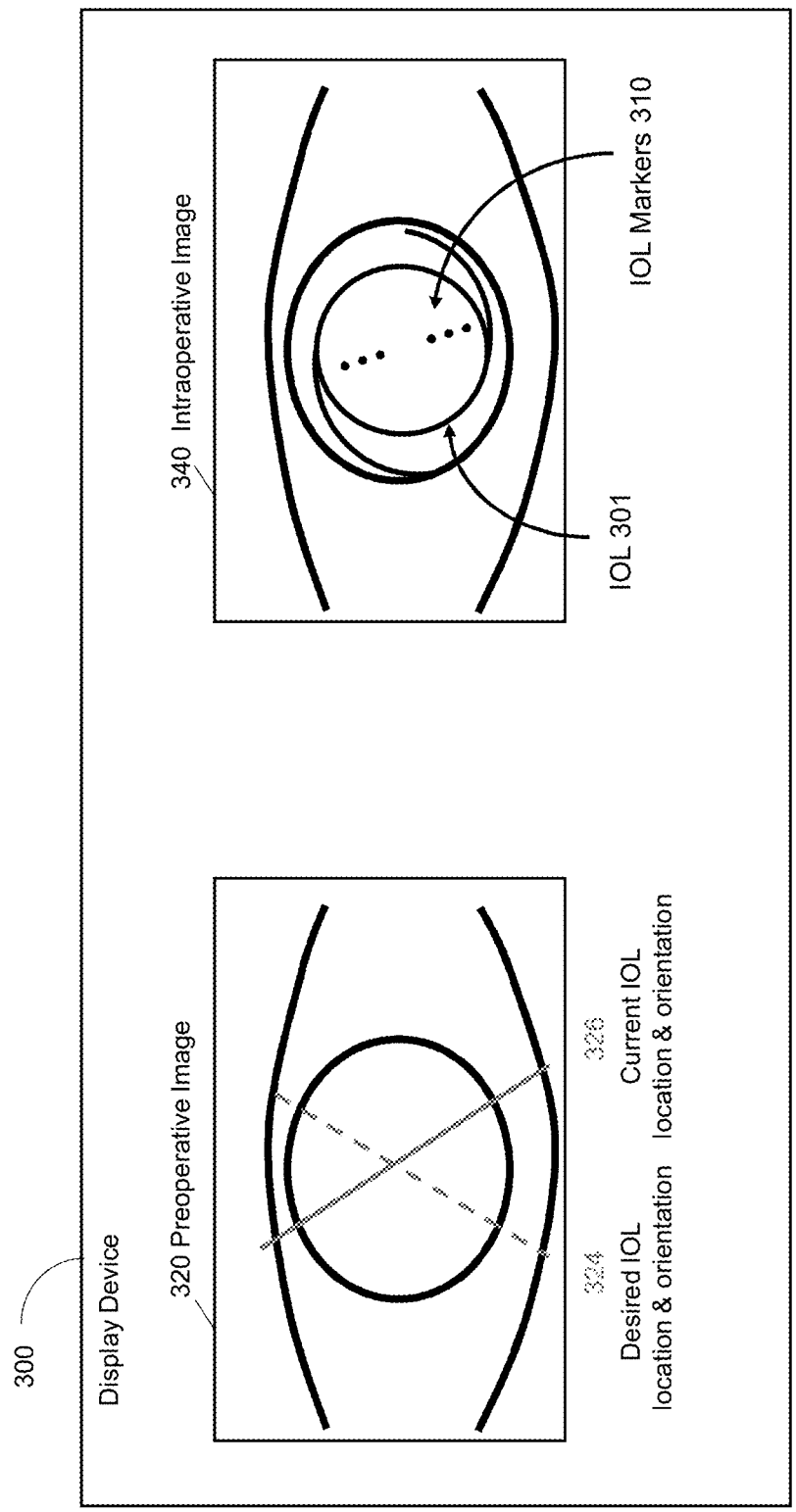
FIG. 3A is a diagram showing an example of a display device showing a preoperative image and an intraoperative image, according to some embodiments of the invention.

FIG. 3A is a diagram showing an example of a display device 300 showing a preoperative image 320 and an intraoperative image 340, according to some embodiments of the invention. As shown in FIG. 3A, the preoperative image 320 shows a desired IOL location and orientation 324 and a current IOL location and orientation 326. The intraoperative image includes IOLs axis marks (or markers) 310 indicating an axis of the IOL. The axis marks may be detected (e.g. by image processing algorithms) in the intraoperative image, and their locations can be copied to the preoperative CS e.g., via the algorithm shown below in FIG. 5, and be used to generate the current IOL location 326.

Figure 3B:
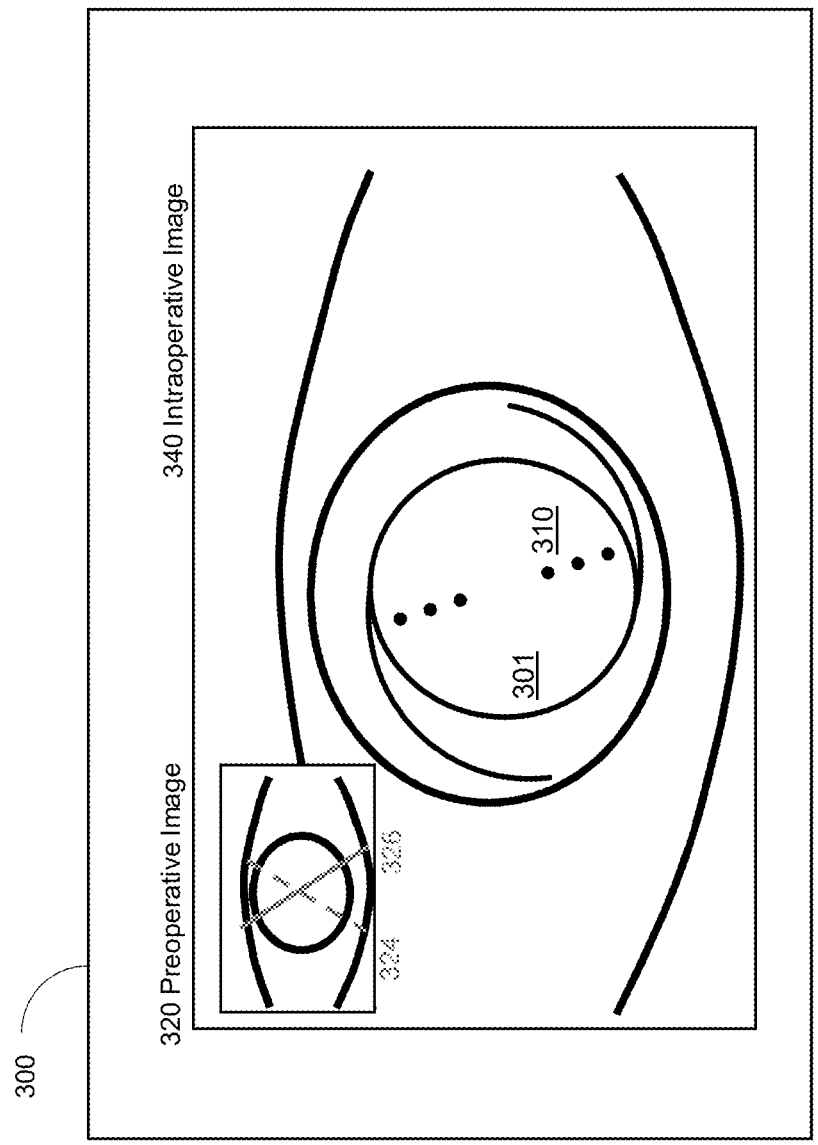
FIG. 3B is a diagram showing an example of a display device showing PIP, according to some embodiments of the invention.

In some embodiments, the preoperative image and the intraoperative image are concurrently displayed in a side-by-side layout, as in FIG. 3A. In some embodiments, for a medical procedure involving an IOL, the preoperative image including a desired and a current IOL alignment and the intraoperative image are concurrently displayed as a "Picture-in-Picture" (PIP). FIG. 3B is a diagram showing an example of a display device 300 showing PIP, according to some embodiments of the invention. The PIP includes the preoperative image 320 showing a desired IOL location and orientation 324 and current IOL location and orientation 326 (e.g., guidance information) that is the IOL location and orientation in a current medical procedure. In FIG. 3B, the intraoperative image 340 shows an IOL 301. The PIP shows a desired IOL location and orientation 324 and current IOL location and orientation 326 (e.g., guidance information) that is the IOL location and orientation in a current medical procedure. In various embodiments, the preoperative image 320 is positioned at other desired locations within the display device. In some embodiments, the preoperative image 320 is positioned such that the preoperative image and the intraoperative image can be viewed simultaneously. In some embodiments, the intraoperative image 340 is positioned within the preoperative image 320.

In various embodiments, the user can provide an input for positioning the preoperative and intraoperative images relative to each other, selecting the size, magnification, centering and/or other characteristics of each image individually to, for example, allow the user to arrange the images to have an unobstructed view of the relevant part of the patient site of interest. In various embodiments, the preoperative image is displayed within the boundaries defining the area of the intraoperative image, outside of the boundaries defining the area of the intraoperative image or any combination thereof. As is apparent to one of ordinary skill in the art, the preoperative image can be positioned/placed in other locations within the display device.

Figure 3C:
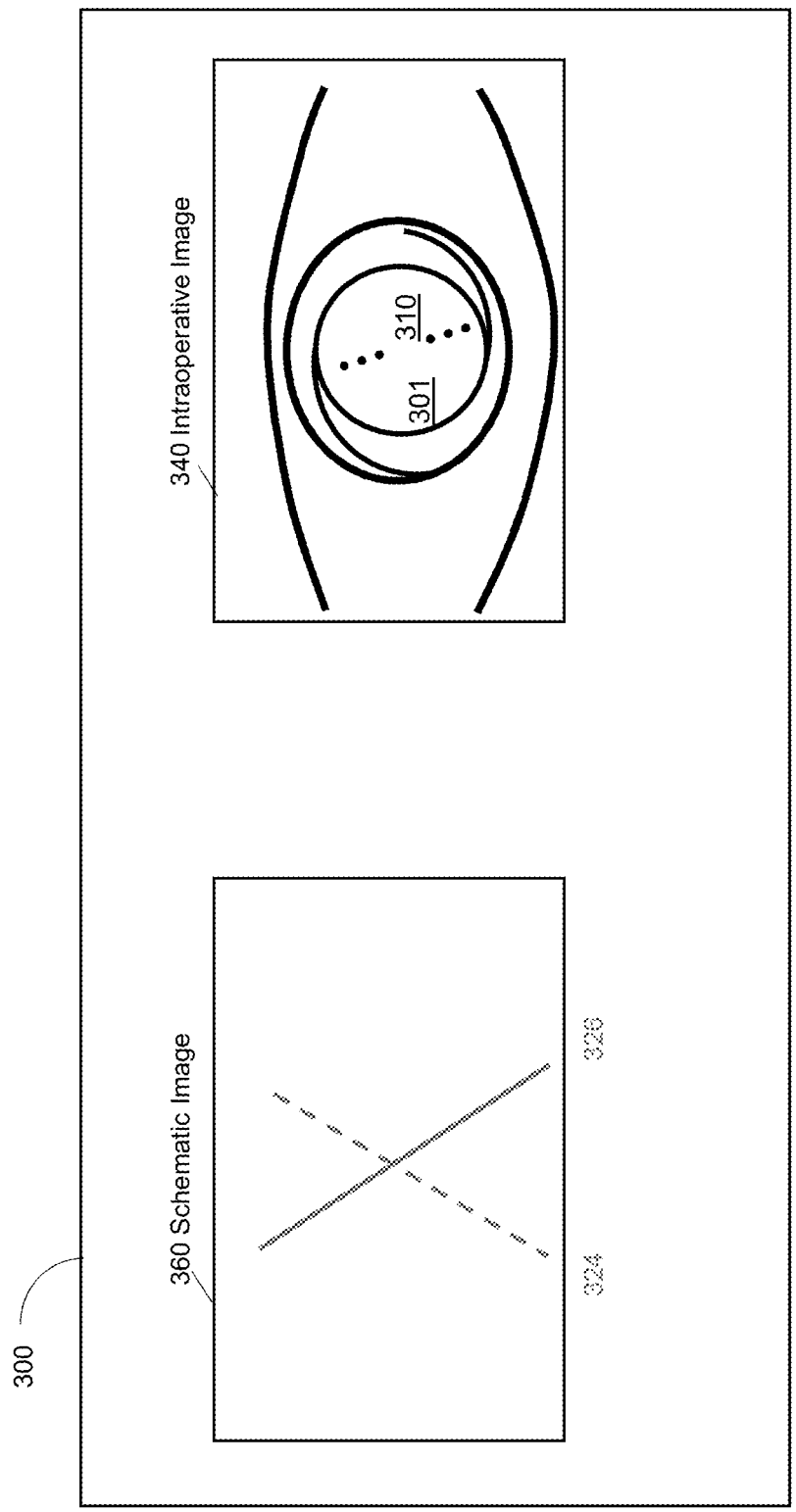
FIG. 3C is a diagram showing an example of the desired and current IOL alignment displayed without the preoperative image, according to some embodiments of the invention.
Figure 4B:
FIGS. 4A-4C are images showing an example of an OCT B-scan located on an intraoperative image, according to an illustrative embodiment of the invention.
Figure 4A:
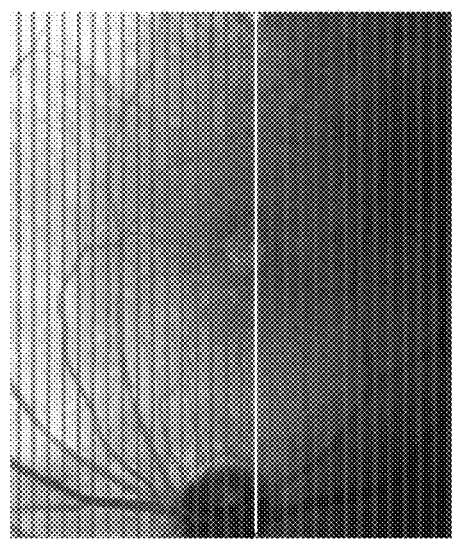
Figure 4C:
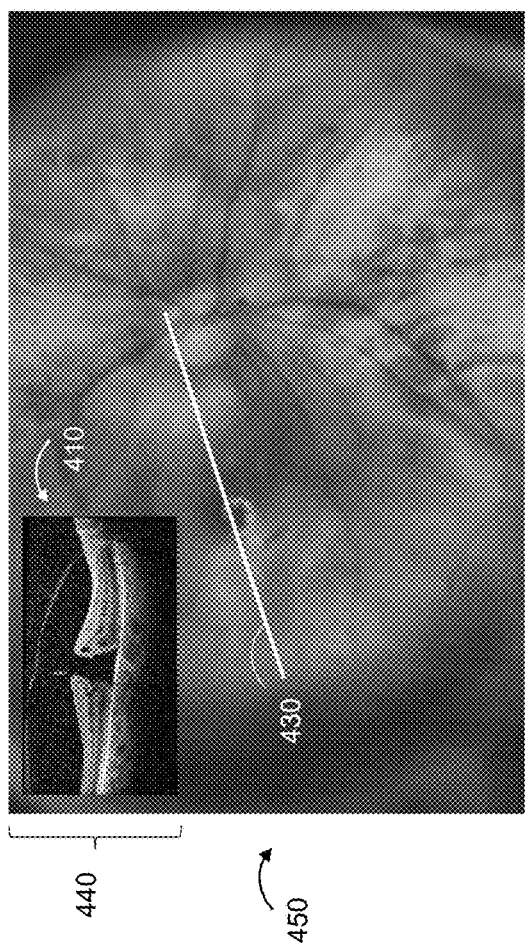

In some embodiments, the indicators for the desired and current IOL alignment are displayed without the preoperative image, as the two indicators can be sufficient for positioning the IOL (e.g., a surgeon may move and/or rotate the IOL until two indicators are aligned, regardless of the background image). For example, turning to FIG. 3C, FIG. 3C is a diagram showing an example of the desired and current IOL alignment displayed without the preoperative image, according to some embodiments of the invention. In some embodiments, the desired and current IOL alignment are displayed are superimposed upon a schematic image (e.g., synthetic representations of an eye, preoperative pupil, center of the pupil). In some embodiments, the first image (e.g, the reference image) is an image of a retina generated by a diagnostic OCT device, accompanied by information regarding the locations, relative to the image of the retina, of OCT B-scans provided by the OCT device. Such location information can be provided as pairs of locations of edges of lines, each line representing an OCT B-scan location with respect to the image of the retina. FIGS. 4A-4C are images showing an example of an OCT B-scan located on an intraoperative image, according to an illustrative embodiment of the invention.

FIGS. 4A and 4B show images generated by an OCT imaging device taken prior to medical procedure (e.g., preoperatively), according to some embodiments of the invention. Image 400 is an image of a retina generated by the OCT imaging device, and image 410 is one of multiple B-scan images generated by the same device. The multiple horizontal lines overlaid on the preoperative image 400 indicate locations on the retina corresponding to each of the multiple B-scans. In some embodiments, the system stores the image of the retina without the overlaid lines, and the location of the lines with respect to the image are stored separately (e.g. as pairs of points indicating the two edges of each line). Line 420 can indicate the location on the retina corresponding to B-scan 410. FIG. 4C shows an intraoperative image 450 of a retina. Preoperative OCT B-scan image 410 is displayed in PIP 440. Using preoperative image 400 of the retina as a reference image (e.g., the image without the overlaid lines is used as reference), the location of line 420 can be copied from the preoperative image 400 to the live image 450, e.g., by copying the location of the two edges of the line from the reference image to the intraoperative image, to generate overlay 430, which can indicate the location on the retina corresponding to the OCT B-scan image 410 displayed in PIP 440. In some embodiments, the user scrolls within the set of B-scan images, and as the OCT B-scan image displayed in PIP 440 changes, the location of the corresponding line on the intraoperative image is determined and displayed as an overlaying line. The determination for the corresponding location on the intraoperative image can be performed on a frame-by-frame basis, even when the preoperative OCT image displayed in PIP 440 has not been changed by the surgeon, as image 450 can be real-time and the overlay can be dynamically updating.

In some embodiments, the preoperative image is a diagnostic image of the retina on which the surgeon made pre-planning notes and markings, and the intraoperative image is a live image of the retina. Pre-planning markings can be for example a location of a membrane that is to be removed during the surgery, and/or a location where a retinal detachment appears. In some embodiments, it can be desirable for a surgeon to view the markings overlaid with the live (e.g., intraoperative) image, e.g., copied or located from the preoperative image to the live image. Copying a marking may be performed by breaking the marking into small line-segments, and copying each of the line edges from the reference image (e.g., the preoperative image) to the target image (e.g., the live image). Each line edge can have a defined location in the image. In general, any shape and color may be represented by locations, e.g. by vertexes, for instance as in an OBJ file. Typically, the overlay is stored separately from the image (e.g., not saved directly on the reference image), using the same CS as the reference image CS, such that the overlay may be copied from the reference image CS to the target image CS.

In some embodiments, one or more still images of a live image is captured by the user, and the overlay appears only on the one or more still images. For example, for procedures where an overlay indicates an area of a detached retina (e.g., a posterior segment ophthalmic procedure) a surgeon may prefer that the overlay does not appear all the time, rather that it appears only responsive to a user-based input received by the display system (e.g. by pressing the footswitch). In some embodiments, this can be preferred since the overlay in some embodiments, can obscure the area that the surgeon needs to attend. In some embodiments, when the image is still (e.g., frozen), the system can add a clear indication or warning so the surgeon is aware that the image is frozen. In some embodiments, the overlay only appears on the live image during a continuous user-based input (e.g. only while the user is pressing down on a footswitch).

Figure 4D:
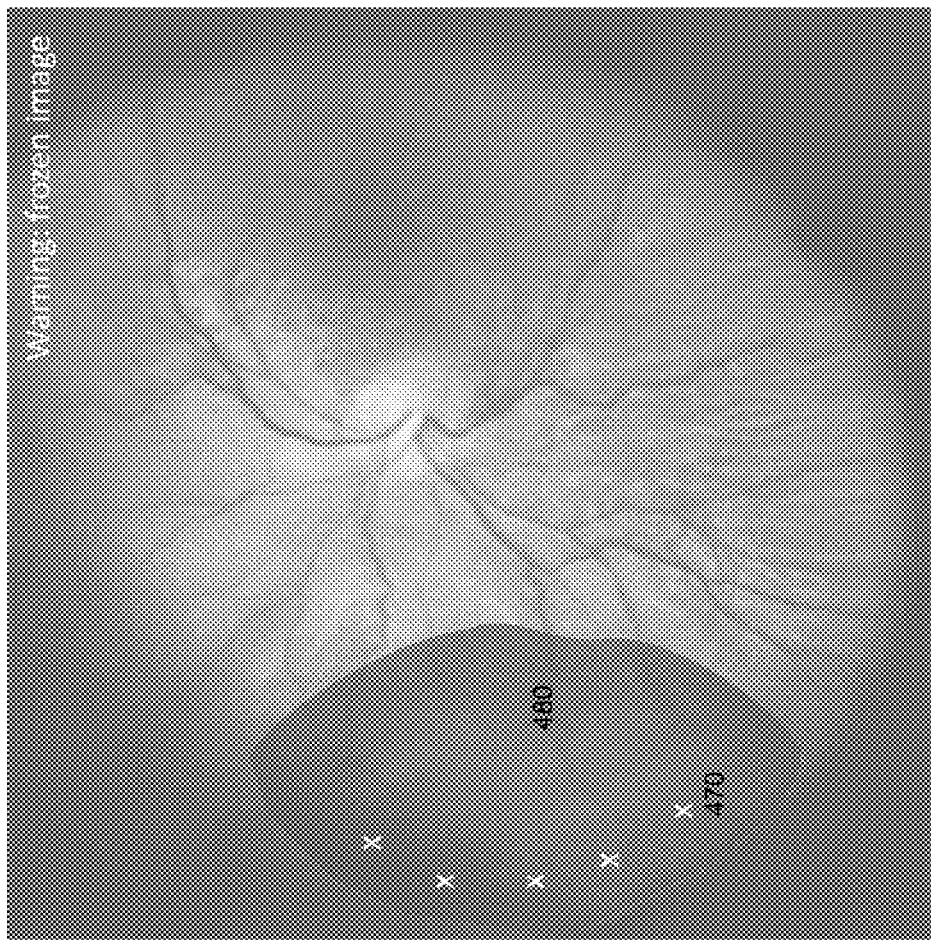
FIG. 4D is an example of displaying an overlay on a still image of an intraoperative image, according to an illustrative embodiment of the invention.

FIG. 4D is an example of displaying an overlay on a still image of an intraoperative image 460 (e.g. when the live image is frozen), according to an illustrative embodiment of the invention. The overlay 480 indicates an area of a detached retina during a posterior segment ophthalmic procedure, e.g. indicated by coloring an area on an intraoperative image of the retina that is detached, and indicating by small crosses 470 locations for laser photocoagulation. Indication 490 is a warning to alert a surgeon that the image is frozen. In some embodiments, displaying the live image frozen with the overlay is time limited, for instance it is shown only when the surgeon presses the footswitch.

In some embodiments, overlaying guidance information on a still image can provide an advantage of avoiding jitter that can arise due to, for example, micro-saccades of the patient's eye and/or due to unstable overlay location on the live image (e.g. instability that is affected by small changes in the live image). For example, overlaying the guidance information on a snapshot can allow for improved verification of an alignment between an IOL and a guidance overlay.

In some embodiments, a still image of a live image is displayed in a side screen or in PIP, and the still image includes the overlay. This can allow the surgeon to see both the live image (e.g., without any obscurations that may interfere with what the surgeon is doing) and the guidance information (overlaid on the snapshot). In some embodiments, two representations of the live image are displayed to the surgeon, one without an overlay and one with an overlay. For instance the live image with the overlay is displayed in a side screen or in PIP. This can allow the surgeon to see both the live image without any obscurations that may interfere with what the surgeon is doing and the live image with the guidance information (overlaid on the live image in PIP).

In some embodiments, for instance in a system for brain surgery, the reference image (e.g., the first image) is rendered from a CT or MRI dataset, from the perspective of the camera that is generating the intraoperative image. In some embodiments, when the user views a stereoscopic (3D) intraoperative image generated by two cameras, a separate reference image is used for copying information to each of the two intraoperative (e.g. live) images. For example, two images can be rendered from a CT or MRI dataset from two perspectives, corresponding to the two perspectives of the cameras generating the live image, or corresponding to the two perspectives of the two optical channels of a surgical microscope, when the user is viewing the patient site of interest via the microscope and not via a display device (or devices). In another example the reference image is a scanning laser ophthalmoscopy (SLO) image generated for instance by a diagnostic OCT device. In yet another example ophthalmic OCT data may be used to generate an en-face image that may be used as a reference image. In another example a reference image may also be generated by an infrared camera, as opposed to imaging in the visible-range.

As described above, guidance information, reference data, or any information can be copied (e.g., transferred or located) from a first image to a second image (or vice versa). The guidance information can be associated with a point in the first image (e.g., a desired IOL marker location), or multiple points in the first image (e.g. a contour of a membrane on the retina represented by a finite number of points). Each point can be copied from the first image to the second image, i.e. a matching location in the second image can be determined for each of the multiple points representing the guidance information.

In some embodiments, a user (e.g., a nurse or a surgeon) verifies that image-to-image location matching is working correctly by moving a cursor (e.g., guidance information) over the first image (e.g. preoperative image), as displayed for instance on a touchscreen of the system side-by-side with the second image (e.g. intraoperative image), to point at prominent image elements, and visually verifying that a corresponding cursor, copied from the first image to the second image, is correctly positioned (e.g., the user may verify that the second cursor points at the same image element in the second image). In these embodiments, the location matching can be performed as shown above in FIG. 5 and/or via registration.

In some embodiments, when image-to-image location matching is based on registering the first image and the second image, a user (e.g., a nurse or a surgeon) verifies that the registration was performed correctly by viewing a toggled view of the first image and second image (e.g. only one of the two images is displayed at any given moment). In these embodiments, the images are displayed such that if one of the images were partially transparent, corresponding anatomical elements in the two images would overlap (e.g. if the registration was performed correctly). In these embodiments, the user views either the first image after it is registered. (e.g. aligned) to the second image, alternately with the second image, or the second image after it is registered (e.g. aligned) to the first image, alternately with the first image. In some embodiments, the user may adjust the toggling frequency. In some embodiments, the user may adjust the registration while viewing the toggled view of the two images. For instance, the user may rotate the registered image such that it is better aligned with other image.

Figure 5:
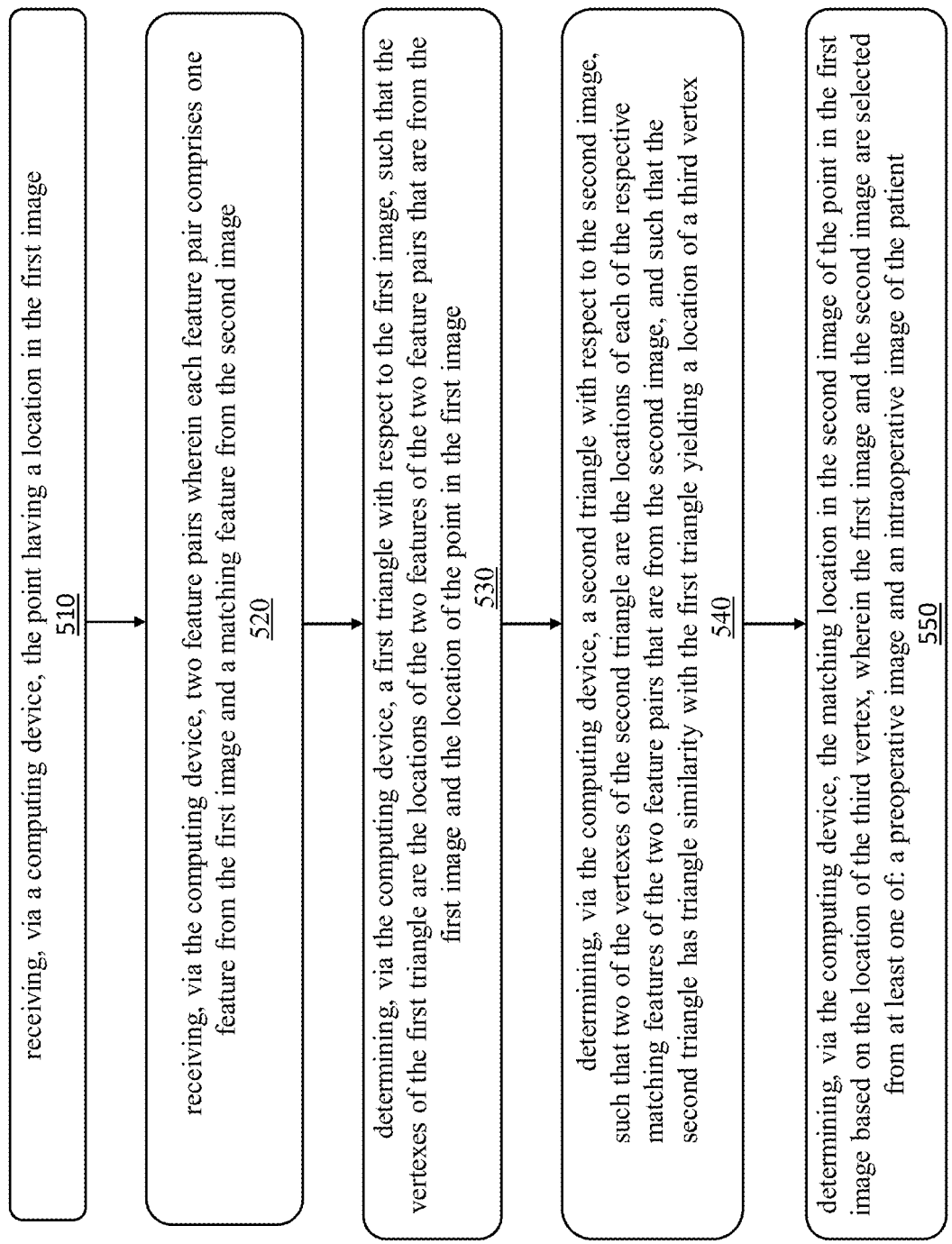
FIG. 5 is flow chart showing a method for determining, for a point in a first image, a matching location in a second image, according to some embodiments of the invention.

FIG. 5 is flow chart showing a method for determining, for a point in a first image, a matching location in a second image, according to some embodiments of the invention.

The method can involve receiving, via a computing device, the point having a location in the first image (Step 510). The point can have a defined pixel location (x,y) where x and y can be integer or non-integer values.

The method can involve receiving, via the computing device, two feature pairs wherein each feature pair comprises one feature from the first image and a matching feature from the second image, wherein each of the features in each feature pair has a corresponding location on its respective image (Step 520). The two feature pairs can be two features pairs from a set of feature pairs. The set of feature pairs can be based on matching features between the first image and the second image. Features can be matched based on similarity between descriptors. In some embodiments, even if features have sufficient similarity between descriptors, they may not actually be a match. In some embodiments, the feature pairs are filtered. The filtering can be based on geometrical relationships, for example, as described in further detail below with respect to FIG. 7 and FIG. 8.

In some embodiments, the two feature pairs are selected from a set of feature pairs, each feature pair includes one feature from a first image and a matching feature from the second image. The two feature pairs can be selected based on distance (e.g., distance measured in pixels) of the two features of the two feature pairs that are from the first image to the point. The distance can be normalized to the size of the anatomy as it appears in the image (e.g., the white-to-white diameter of the eye in the image). The distance can be based on a minimum distance or a maximum distance as input to the system (e.g., by a user, from a file or as a programmable parameter).

For example, assume two feature pairs, FP1a, FP1b, where FP1a has location (X1FP1a,Y1 FP1a) in the first image and FP1b, has location (X2FP1b,Y2 FP1b) in the second image and FP2a. FP2b, where FP2a has location (X1FP2a,Y1 FP2a) in the first image and FP2b, has location (X2FP2b,Y2 FP2b) in the second image.

The method can involve determining, via the computing device, a first triangle with respect to the first image, such that the vertexes of the first triangle are the locations of the two features of the two feature pairs that are from the first image and the location of the point in the first image (Step 530). Continuing with the above example, the vertexes of the first triangle are (X1FP1a,Y1 FP1a), (X1FP2a,Y1 FP2a), and (x,y), the location of the point.

The method can involve determining, via the computing device, a second triangle with respect to the second image, such that two of the vertexes of the second triangle are the locations of each of the respective matching feature of the two feature pairs that are from the second image, and such that the second triangle has triangle similarity with the first triangle yielding a third vertex (Step 540). Continuing with the above example, the two vertexes of the second triangle are (X2FP1b,Y2 FP1b), (X2FP2b,Y2 FP2b). With the three vertexes of the first triangle known, angles of the first triangle, the lengths of each side of the first triangle and/or other geometrical characteristics of the first triangle can be determined. With the known angles and/or known lengths of each side and/or other known geometrical characteristics for the first triangle, the third vertex of the second triangle can be determined by finding a similar triangle to the first triangle. In some embodiments, the second triangle can be constructed (e.g., virtually) by connecting the two matching features and drawing (e.g., virtually) two lines (e.g., rays) originating in each of the second triangle features and based on the known angles of the first triangle that correspond to each of the two features. The crossing point of the two lines can determine the third vertex of the second triangle and can define the third vertex. In various embodiments, determining the second triangle that has similarity with the first triangle is done, as is known in the art.

In some embodiments, an order of the vertices in the second triangle proceeding clockwise is the same as the order of their respective matching vertices in the first triangle proceeding clockwise. In some embodiments, the second triangle is not flipped with respect the first triangle such that the second triangle is not a mirror image of the first triangle. In some embodiments, each vertex angle in the second triangle is equal to the vertex angle of its respective matching vertex in the first triangle. For example, assume feature pair (F1, F2), where F1 is a vertex in the first triangle and F2 is a vertex in the second triangle. Assume also that F1 is a vertex having an associated angle of 30 degrees. Then F2 is a vertex in the second triangle that also has an associated angle of 30 degrees. In this manner, the angles associated with the vertices in the first triangle are preserved for the corresponding vertices in the second triangle.

The method can involve determining, via the computing device, the matching location in the second image of the point in the first image based on the location of the third vertex (Step 550). In some embodiments, the matching location in the second image can be set to the location of third vertex. As is apparent to one of ordinary skill in the art, a triangle does not actually need to be drawn, it can be virtually constructed and the properties (e.g., angles, lengths, and/or any triangle properties and/or characteristics) can be stored within the computing device.

In some embodiments, the method can involve repeating the determination of the point to be located using multiple triangles and determining the final result by averaging the multiple results.

As is apparent to one of ordinary skill in the art, the discussion with respect to FIG. 5 is with respect to one point, however, in various embodiments, the method steps of FIG. 5 can be applied to multiple points. For example, in the case of a line indicating a desired orientation of an IOL with respect to a preoperative image, two or more points along the line (e.g. the two edges of the line) can be selected to represent the line, and each of these points may be copied to (or located in) the CS of the intraoperative image. For each copied point, the feature pairs can be updated (e.g. different feature pairs are used to copy each point). Thereafter, a line may be generated in the CS of the intraoperative image, e.g. by connecting the copied points.

Figure 6A:
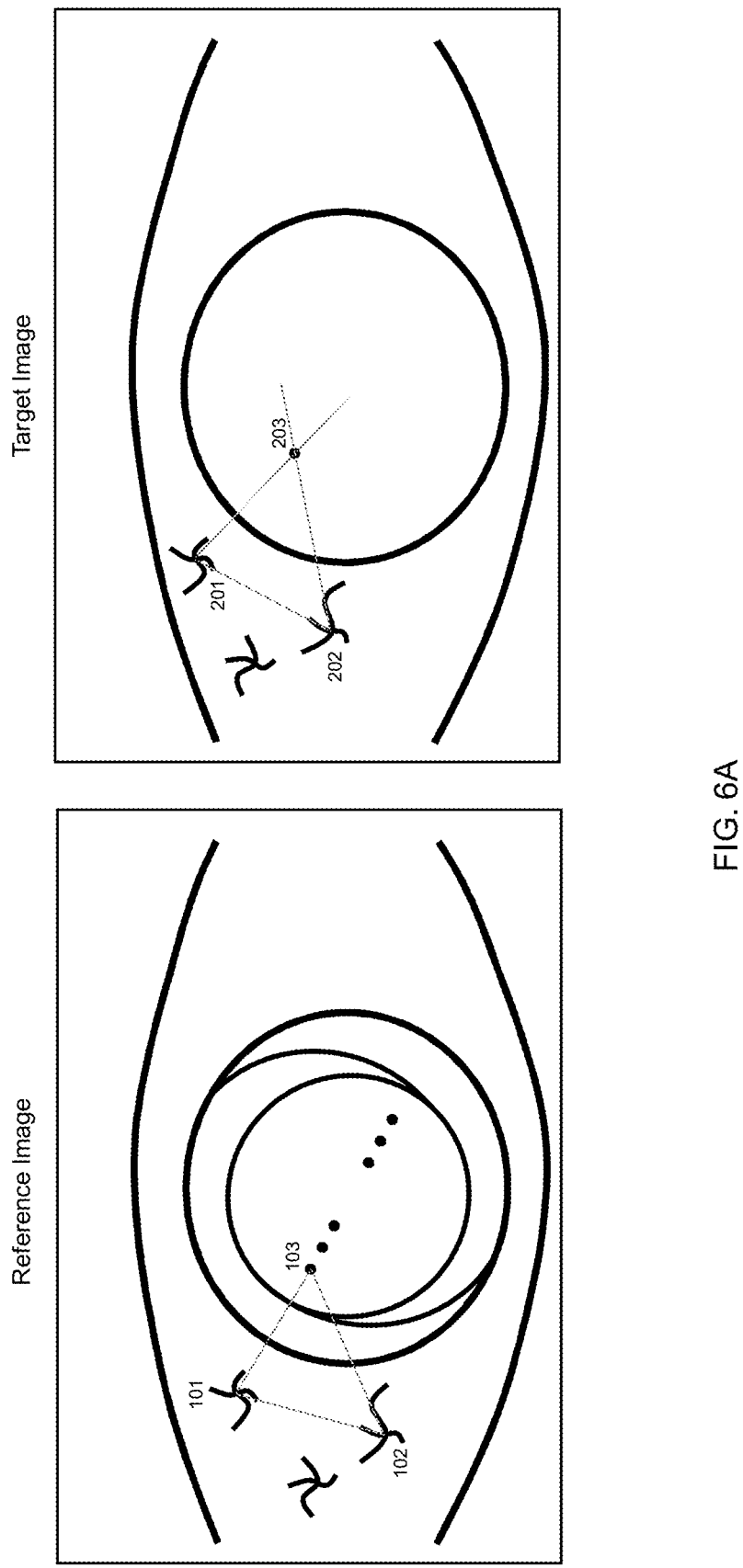
FIG. 6A is a diagram showing an example of a point in a first image being copied to a second image using the method of FIG. 5, as described above, according to some embodiments of the invention.

FIG. 6A is a diagram showing an example of a point in a first image (e.g., a preoperative image, intraoperative image or a reference image) being copied to a second image (e.g., a preoperative image, an intraoperative image or a target image) using the method of FIG. 5, as described above, according to some embodiments of the invention. As shown in FIG. 6A, the first image is an intraoperative image having point 103, the second image is a preoperative image. The point 103 is copied onto the preoperative image via the method as described in FIG. 5 (e.g., by locating the point on the preoperative image). In FIG. 6A the point is an IOL axis mark. A first triangle is constructed having features 101 and 102, and point 103 as the vertexes. Features 101 and 102 are the features in the first image from the received two feature pairs (e.g., as determined/selected from among a set of feature pairs for the two images). Features 201 and 202 are the features in the second image from the received two feature pairs. Features 101 and 201 comprise one feature pair (i.e. they are matching features), and features 102 and 202 comprise a second feature pair. A second triangle similar to the first triangle is constructed in the second image, as described above with respect to FIG. 5. In this manner, vertex 203 (e.g., the third vertex of the target triangle) in the second image is matched to point 103 in the first image, or in other words in this manner point 103 is accurately copied (e.g., transferred) from the first image to the second image.

Figure 6B:
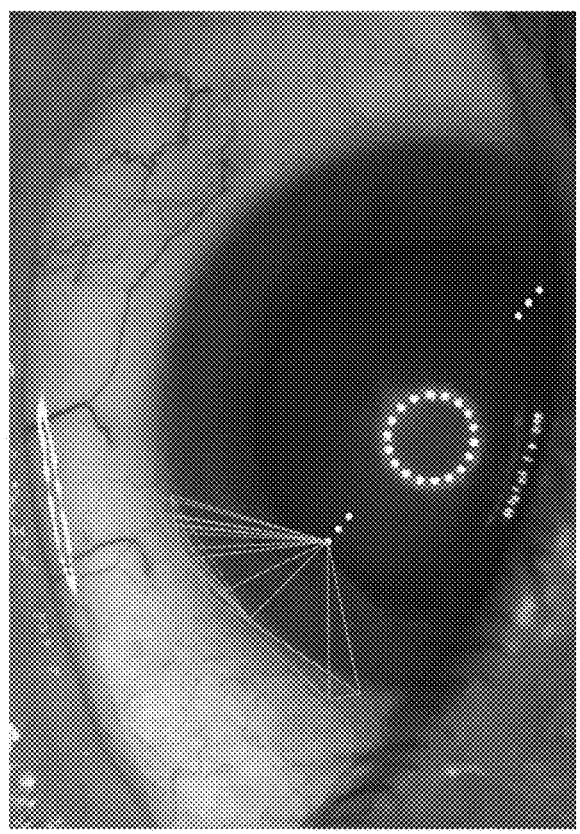
FIG. 6B shows images of an example of copying a location between two actual images of an eye, according to illustrative embodiments of the invention.
Figure 6B:
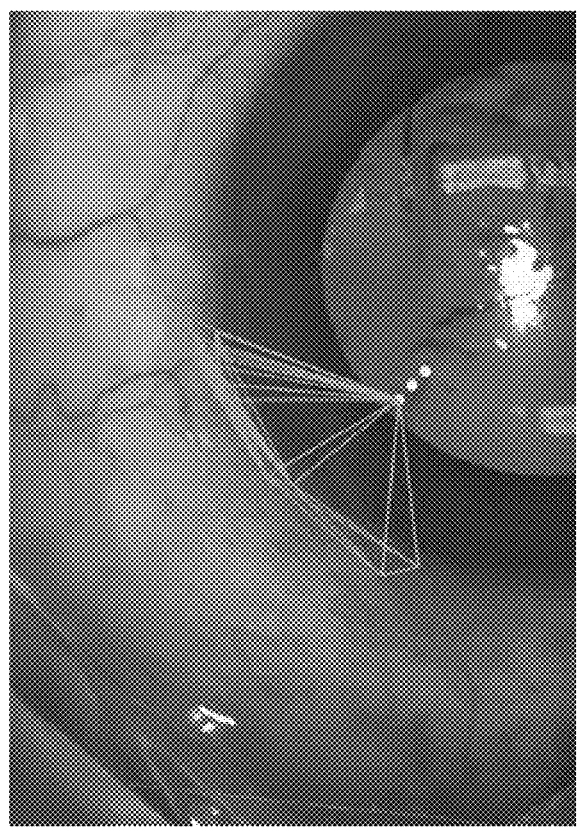

FIG. 6B shows images of an example of copying a location between two actual images of an eye, according to illustrative embodiments of the invention. In FIG. 6B, the reference image is an intraoperative image and the target image is a preoperative image. The intraoperative image is sampled before IOL insertion and the reference point is arbitrarily chosen (e.g., three dots are depicted in this example to exemplify three axis marks). In this example multiple triangles are constructed for copying a single location. In some embodiments, the resulting multiple target locations are averaged to generate an averaged target location. In some embodiments, the multiple target locations can be filtered such that all outlier target locations are filtered out. The outlier target locations can be, for example, all target locations that are more than a maximum distance from an average target location. In some embodiments, feature-pairs that have been used to calculate the outlier target locations (e.g. by constructing similar triangles in the first and second images) are identified, and any target location that was calculated based on these features pairs (e.g. and was not already filtered out) is also filtered out. This can improve the accuracy of the averaged target location.

In some embodiments, the method described in FIG. 5 is modified such that it is not a triangle that is used to copy the at least one location, but another geometric relationship. The geometric relationship can be a relationship that is scale and rotation invariant. For example, similar triangles can stay similar irrespective of scale or rotation of the one image relative to the other. In various embodiments, the geometric relationship is a mathematical formula. For example, a mathematical formula that given three xy locations generates a fourth xy location. In various embodiments, the geometric relationship can be a circle, square, hexagon, octagon and/or any geometric shape as is known in the art. In some embodiments, more than two features are used to create the geometric shape. For example, three features may be used, together with the point, to generate a quadrilateral in the first image, and a similar quadrilateral may be constructed in the second image (e.g. based on the three corresponding matching features) to determine the matching point in the second image. In some embodiments, more than one instance of each shape is used. For example, an intersection of three circles may define a location, each circle being defined by two reference features and the reference location.

Figure 7:
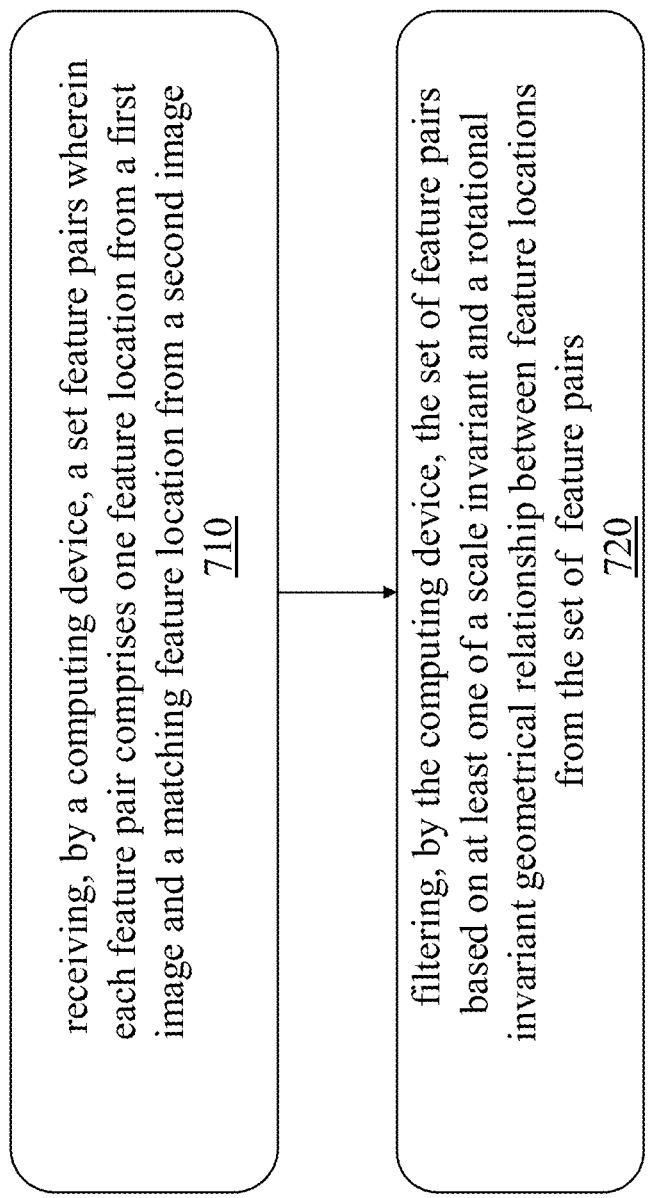
FIG. 7 is a flow chart showing a method for determining a set of feature pairs between features of two images, according to some embodiments of the invention.

As described above, feature pairs and/or a set of feature pairs can be determined between two images. FIG. 7 is a flow chart showing a method for determining a set of feature pairs between features of two images, according to some embodiments of the invention. The method can involve receiving, by a computing device, a set of feature pairs, each feature pair including one feature location from a first image and a matching feature location from a second image (Step 710).

In some embodiments, a first set of feature from a first image and a second set of feature are received, and the set of feature pairs are determined. In these embodiments, the first set of features and/or the second set of features can be determined as is known in the art. For example, the first set of features and/or the second set of features in the images can be detected by deep learning. The first set of features and/or the second set of features can be detected within their respective images and described by feature detection algorithms, as is known in the art. Each feature can have a defined point location (e.g., a location having sub-pixel resolution) and a descriptor, a vector of values which describes the image patch around the interest point.

Features between two images (e.g. two images of the same scene) can be matched, for example based on their similarity (e.g., the similarity of the descriptors of the features). Features between two images may be matched even if the two images are not exactly the same. For example, in a cataract procedure, the preoperative image and the intraoperative image of the eye may be different, yet numerous matching image elements are apparent in both images, such as elements in the iris and junctions of blood vessels. As is known in the art, matching features based on the similarity of their descriptors does not guarantee that the matching is valid. Indeed, in some cases many, or even the majority of matched pairs of features between two images are false. For example, when pairing features from two different images of the same house, two features detected at the corners of two different windows may be falsely paired due to the similarity of the windows. Various algorithms are known in the art for detecting features and for generating descriptors, such as SIFT, SURF, and other. Descriptors may also be generated via deep learning, as known in the art.

The method can involve filtering, by the computing device, the set of feature pairs (Step 720). In some embodiments, the set of feature pairs can be filtered based on a predefined geometrical relationship between feature locations from the set the feature pairs. For example, in some scenarios, a set of feature pairs can be received or some prior art methods for feature matching can generate a list of feature pairs with false pairs. Filtering the set of features pairs can result in a set of feature pairs that has less features pairs then the received and/or generated set of feature pairs. Filtering the set of features pairs can result in reducing false features pairs in the set of features pairs.

A set of feature pairs can be filtered by evaluating a geometrical relationship between features. The geometric relationship can be scale and rotation invariant. The geometric relationship can be based on a Euclidean distance (e.g., in pixels) between any two features in an image. The ratio of a reference distance (e.g., a distance between two features in the reference image) to a matching target distance (e.g., a distance between the two matching features in the target image) can be approximately equal to the relative scale of the two images, That is, if any two pairs of features that were correctly paired are used to calculate such a ratio, then the resulting ratio can be more or less the same. By calculating the ratio for all the possible couples (or substantially all) of the pairs in the two images (e.g., for instance using all the pairs in the pair list that were not filtered out by earlier methods, e.g. methods based on the descriptor similarity score), and even without knowing the actual relative scale of the two images, the actual scale can stand out, for instance in a histogram of all the resulting ratios. Feature pairs that are used in the calculation of ratios around the correct scale may be identified and other feature pairs may be filtered out (e.g. discarded from the set of feature pairs). In some embodiments, additional filtering is performed based on other geometric relationships, for instance by using triplets of feature pairs and comparing the similarity of triangles they define. In some embodiments, the additional filtering is performed by using at least three feature pairs and comparing similarity of polygons they define in the two images. In some embodiments, similarity can be similarity up to a predefined tolerance. The filtering can include discarding form the set of feature pairs at least one feature pair of the at least three feature pairs when the polygons are non-similar.

In some embodiments, a geometric relationship for filtering outliers may be for example based on the angle of the line connecting any two features in an image. For example, the angle of the line connecting a feature in location (100, 100) and a feature in location (200, 100) is 0 (e.g., where locations are in pixel values). The angle of the line connecting a feature in location (100, 100) and a feature in location (200, 200) is 45 degrees. The difference between a reference angle (e.g., an angle of a line connecting two features in the reference image) to a matching target angle (e.g., an angle of a line connecting the two matching features in the target image) be approximately equal to the rotation between the two images. In some embodiments, if any two pairs of features that were correctly paired can be used to calculate a difference of angles, then the resulting difference can be more or less the same. By calculating this difference for all the possible couples of pairs in the two images (e.g., using all the pairs in the pair list that were not filtered out by earlier methods, e.g. methods based on the descriptor similarity score), and even without knowing the actual rotation of one image compared to the other, the actual rotation can be visible in a histogram of all the resulting differences. Feature pairs that were used in the calculation of angle differences around the correct rotation can be identified and other feature pairs can be filtered out.

Figure 8B:
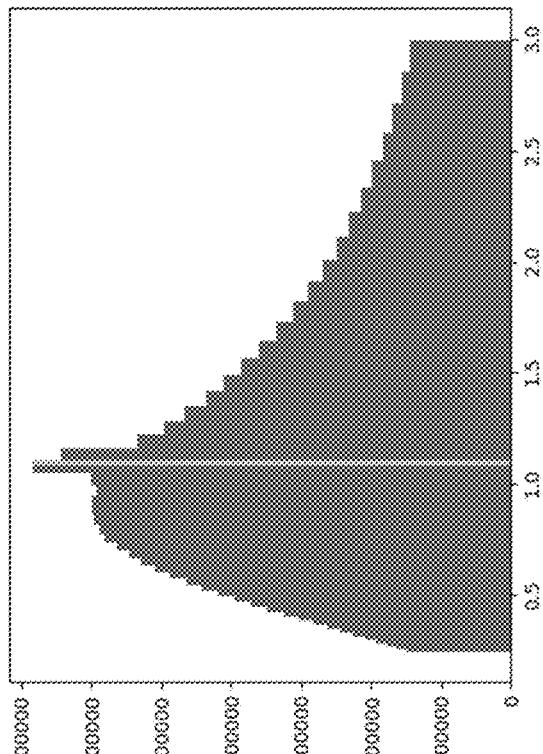
FIG. 8B are diagrams that illustrate two histograms of ratios generated from actual images of a retina, according to some embodiments of the invention.
Figure 8A:
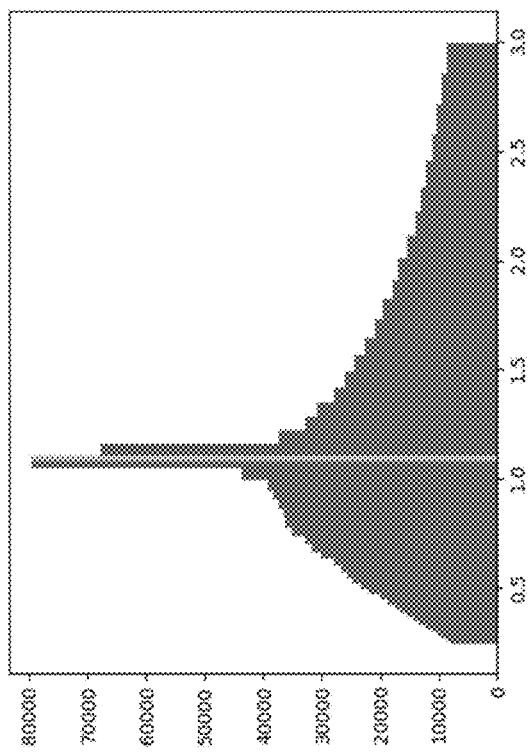
FIG. 8A shows a geometrical relationship being used to filter a set of feature pairs, according to some embodiments of the invention.
Figure 8A:
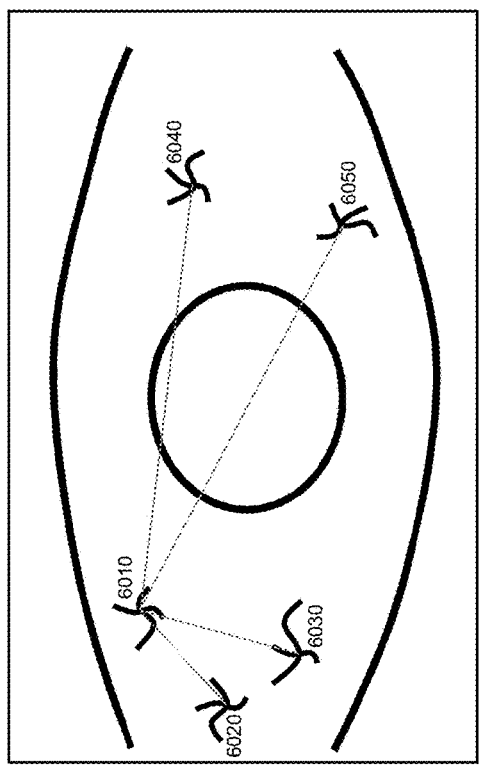
Figure 8A:
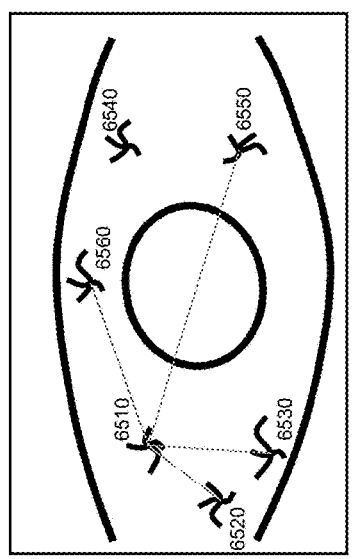

FIG. 8A shows how geometrical relationship can be used to filter a set of feature pairs, according to some embodiments of the invention. Five vessel junctions associated with features 6010-6050 are illustrated in the reference image (top). Six blood vessel junctions associated with features 6510-6560 are illustrated in the target image (bottom).

Assume a pairing algorithm (e.g., based on the similarity of descriptors) correctly paired the features to create a set of feature pairs as follows: 6010 and 6510, 6020 and 6520, 6030 and 6530, and 6050 and 6550. Also assume features 6040 and 6560 were incorrectly paired, and thus is an false feature pair in the set of feature pairs. In accordance with the method described in FIG. 7, the set of feature pairs can be filtered. In some embodiments, an outlier filtering algorithm (e.g., algorithm to filter erroneous pairs) designed to detect erroneous pairs (e.g. false feature pairs) as described above can calculate the distances between the various couples of features in each image, and calculate the ratio of distances between matching pairs. For example, a distance between 6010 and 6020 in the reference image can be divided by the distance between 6510 and 6520 in the target image, and the result is 1.39. In this example, all of the calculated ratios based on correctly matched features are around 1.4, which is the relative scale between the two images. Ratios involving the outlier pair (6040, 6560) can generate other results. The algorithm may then conclude that this pair is incorrect and filter it out of the list of pairs. Note that the ratios are not expected to be exactly 1.4 due to the various reasons discussed earlier that render the use of a global fit non-optimal (e.g. distortions in the live image).

The features in the reference image and the target image are automatically detected, and in general they are not necessarily associated with the center of a blood vessel junction, and/or they are not associated with any image element that can be identified by a naked eye.

FIG. 8B are diagrams that illustrate two histograms of ratios generated from actual images of a retina, according to some embodiments of time invention. The histograms peak at the relative scale in this case, about 1.1. The majority of the histogram, excluding the peak, is generated by incorrectly paired features, and this distribution of ratios may be expected for random incorrect pairing. The histogram can demonstrate the strength of this filtering method, as it can allow to easily filter out the incorrect pairs even when the number of inliers (e.g., correct pairs) is small, simply by identifying which pairs more frequently contribute to the histogram bins around the peak and which pairs more frequently contribute to other histogram bins. The two histograms in this example are generated based on the same two images.

The initial list of feature pairs can be generated by matching all the features detected in one image with features in the second image based on finding the feature with the most similar descriptor (e.g., first runner-up). The top histogram was generated after the initial list of feature pairs was initially filtered by taking only pairs where the first runner-up descriptor similarity score was significantly higher than the second runner-up descriptor similarity score (e.g., with a 0.9 score ratio threshold).

In this example, the number of pairs after this filtering stage was 1667. The total number of calculated distance ratios in the histogram is thus 1667*1666/2. Based on this histogram, 66 feature pairs were identified as the most frequent to contribute to the peak bins. In this example, the pair that contributed the most to the peak bin was identified, and only pairs that contributed at least 80% of this pair's contribution survived the filtering. As mentioned above, further filtering based on triplets of pairs may eliminate the very few outliers that survive this stage, if it is required. In this example, only 2 were further filtered, leaving 64 verified pairs.

The bottom histogram was generated without any initial filtering. All the features that were detected in one image (in this case 9396 features) are matched with features in the second image (7522 features, e.g., "double booking" was allowed), totaling with 9396 pairs. Based on this histogram, 143 feature pairs were identified as the most frequent to contribute to the peak bins when using the 80% threshold as above, and 395 were identified when using a 50% threshold.

In various embodiments, the filtering of feature pairs can be implemented either on the entire image or on separate image tiles. When used on the entire image, the peak in the histogram can be slightly wider than when used in tiles, due to fact that the two images are not perfectly identical (e.g., even if scale, rotation and translation were to be corrected), as described earlier. Implementing the filtering method in tiles can involve generating several separate histograms using features belonging to several smaller areas (e.g., tiles) in the reference image (e.g., together the tiles cover the entire image, and an overlap is allowed between tiles). Since local features (e.g., features belonging to the same area in the image) can be assumed to be affected by common image distortions, the histograms generated locally can exhibit narrower peaks. In some embodiments, an initial set of filtered pairs is identified on the entire image and are used to define corresponding tiles between the images, for instance by calculating the corresponding locations of tile corners in the second image (e.g., by using the triangles similarity method as described above in FIG. 5). Once corresponding tiles are identified, features may be detected and paired separately in each pair of corresponding tiles in both images, thus increasing the total number of verified pairs.

In some embodiments, a second feature pair search is performed within an area of each filtered feature pair. In these embodiments, the filtering of the feature pairs in the second round can be less limiting than the original filtering such that the total number of filtered pairs can increase.

In some embodiments, any feature pairs comprising features that may be regarded as unreliable reference features for image-to-image location matching during a procedure are excluded from being included in the feature pair set. For example, during anterior segment ophthalmic surgery, any feature pairs that are not part of the limbus, or within a certain distance of the limbus, may be regarded as unreliable reference features for image-to-image location matching, and may be excluded from being included in the feature pair set.

In some embodiments for anterior segment ophthalmic surgery, blood vessels are classified to scleral vs. conjunctival, and feature pairs that are associated with conjunctival blood vessels are excluded from the feature pair set. A feature pair is associated with conjunctival blood vessels for instance when one of the two features (e.g. the feature from the live image) is within a predetermined distance of blood vessels that were classified as conjunctival. The classification may be implemented, for instance, based on image sequences at the initial stage of the surgery, e.g. by implementing image processing algorithms and/or deep learning algorithms.

In some embodiments, once features are detected in both images and a set of filtered feature pairs is generated, the locations of the features in the live image are tracked. Tracking features may be implemented for instance by template matching between consecutive frames in the live image sequence, where the templates are small image patches around the features, and the searching area in the current frame is limited to the area around the feature location in the previous frame. In some embodiments, the process of detecting features and determining feature pairs; is repeated during the procedure, and the features are tracked until a new set of feature pairs is determined. In some embodiments, the process of detecting features and determining feature pairs is repeated during the procedure at a predetermined frequency. Repeating this process can eliminate or substantially eliminate errors in feature tracking.

In some embodiments, the set of feature pairs includes features that cover an entire region of interest for a guided surgical procedure. For example, for an anterior segment ophthalmic surgery, in some embodiments, it can be advantageous that the features used are not all concentrated in one side of the eye, and instead they are substantially uniformly distributed around the limbus area. A uniform coverage can guarantee that local triangles are constructed even when some parts of the limbus area are hidden, e.g. by tools, and/or when some parts are distorted, e.g. due to hemorrhages or liquids on the eye.

In some embodiments, preoperative images exhibit an eyelid partially covering the limbus, rendering feature detection impossible in the covered areas. This can decrease the robustness of the triangle similarity method during surgery. In some embodiments at the beginning of the procedure a "proxy" image can be saved. The proxy image can be an intraoperative image, saved prior to the beginning of the guided procedure. The overlay location can be copied from the preoperative image CS to the proxy image CS using the triangle similarity method (e.g., as describe above with respect to FIG. 5), and later in the procedure the proxy image can be used as a reference image for copying the overlay to the live image. In this manner, guidance information can be copied between two intraoperative images.

In some embodiments, the preoperative image is registered with the proxy image and overlay location can be copied from the preoperative image CS to the proxy image CS based on the determined transformation between the images. In some embodiments, using a proxy image can be advantageous also in other scenarios (e.g., other than anterior segment ophthalmic surgery).

Figure 9:
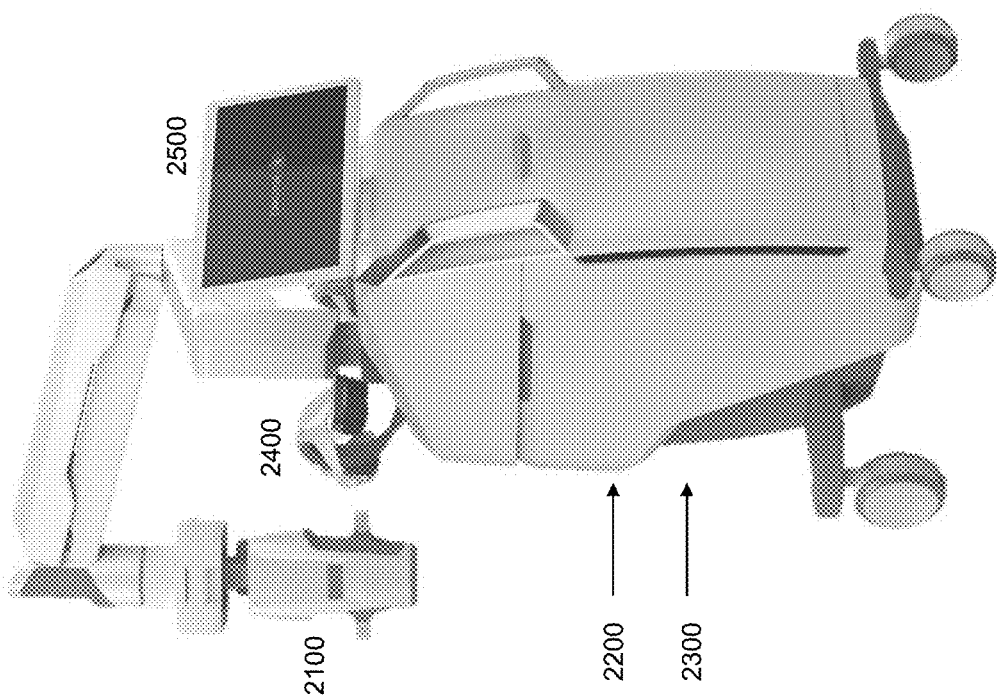
FIG. 9 is a diagram of an example of a system for overlaying guidance information, according to some embodiments of the invention.
Figure 9:
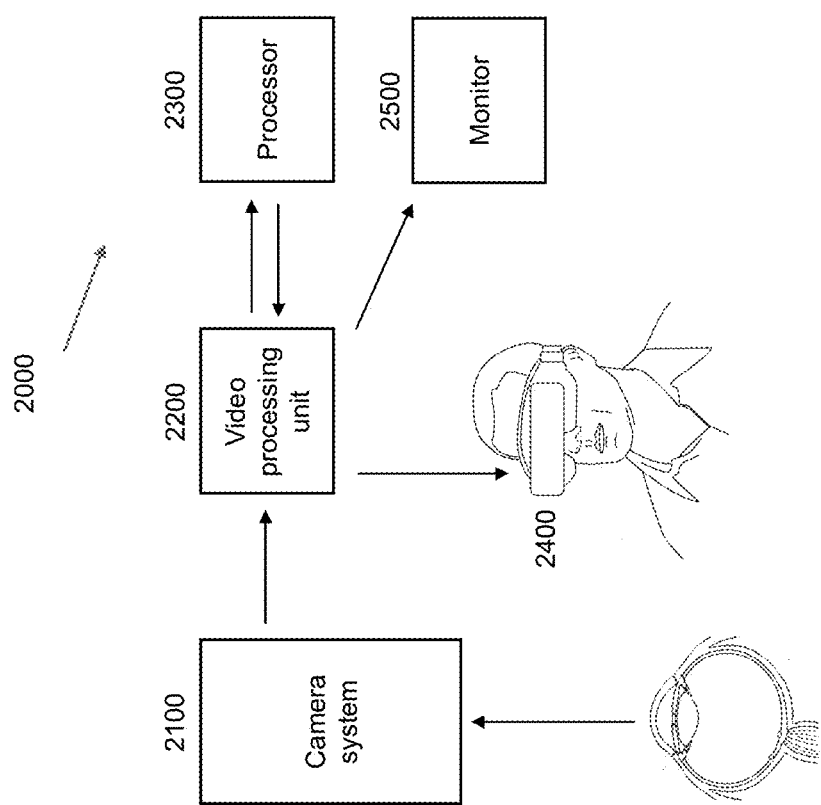

FIG. 9 is a diagram of an example of a system 2000 for overlaying guidance information, according to some embodiments of the invention. The system can include a camera system 2100 (e.g. a stereoscopic camera system), a video processing unit 2200 (e.g. embedded hardware), a processor 2300 (e.g. a PC), a head wearable display (HWD) 2400, and a monitor 2500.

During operation, the video processing unit 2200 can receive and read images from cameras in the camera system 2100, process the images, and stream the processed images to the HWD 2400 and/or the monitor 2500. The processing of the images can involve standard image processing (e.g. de-Bayer, automatic gain control, distortion correction), adding images in PIP view or in side-by-side view, and/or overlaying guidance information, e.g. as guidance symbols.

In some embodiments, the monitor 2500 is a 3D monitor. The 3D monitor can be viewed with special glasses to see a 3D image.

In some embodiments, the system 2000 includes up to three HWDs 2400 that can simultaneously display a live image. The images displayed via the three HWDs can be the same or different. For example, a supervising surgeon may zoom out, freeze the image and/or use menus for drawing markings on the image, while at the same time the resident is viewing the live image without any change. In some embodiments, the images have varying magnifications, e.g. when the magnification is digital.

In some embodiments, the camera system 2100 is assembled on a standard surgical microscope (not shown). In some embodiments, the camera system 2100 replaces the microscope oculars. In some embodiments, the system 2000 includes both the camera system 2100 and microscope oculars. In these embodiments, beam-splitters can be used to partially deflect the optical images towards the cameras. In some embodiments, the camera system 2100 has a single camera. In some embodiments, the camera system has a stereoscopic camera (e.g., two cameras).

In some embodiments, when the camera system 2100 is assembled on a standard surgical microscope, in addition to or instead of overlaying the guidance information on an image displayed via an HWD and/or a monitor, the guidance information may be superimposed on the optical image viewed through the oculars (e.g., beam-splitters may be used to deflect the overlay images towards the oculars). In these embodiments, the overlay images can include the guidance information on a black background, such that only the guidance information is superimposed on the optical image generated by the surgical microscope, and other areas in the overlay images do not obscure the optical image. The overlay image (or images) can be generated based on the image (or images) captured by the camera (or cameras) of the camera system, for instance using the image-to-image location matching method as described above with respect to FIG. 5. The overlay images in these embodiments can require a correction for allowing the overlay to be accurately superimposed on the optical image viewed via the oculars. The correction can be based on a predetermined alignment between the camera and the corresponding optical image as viewed via the ocular (e.g. that takes into consideration also the different optical distortions of the two channels).

Figure 10:
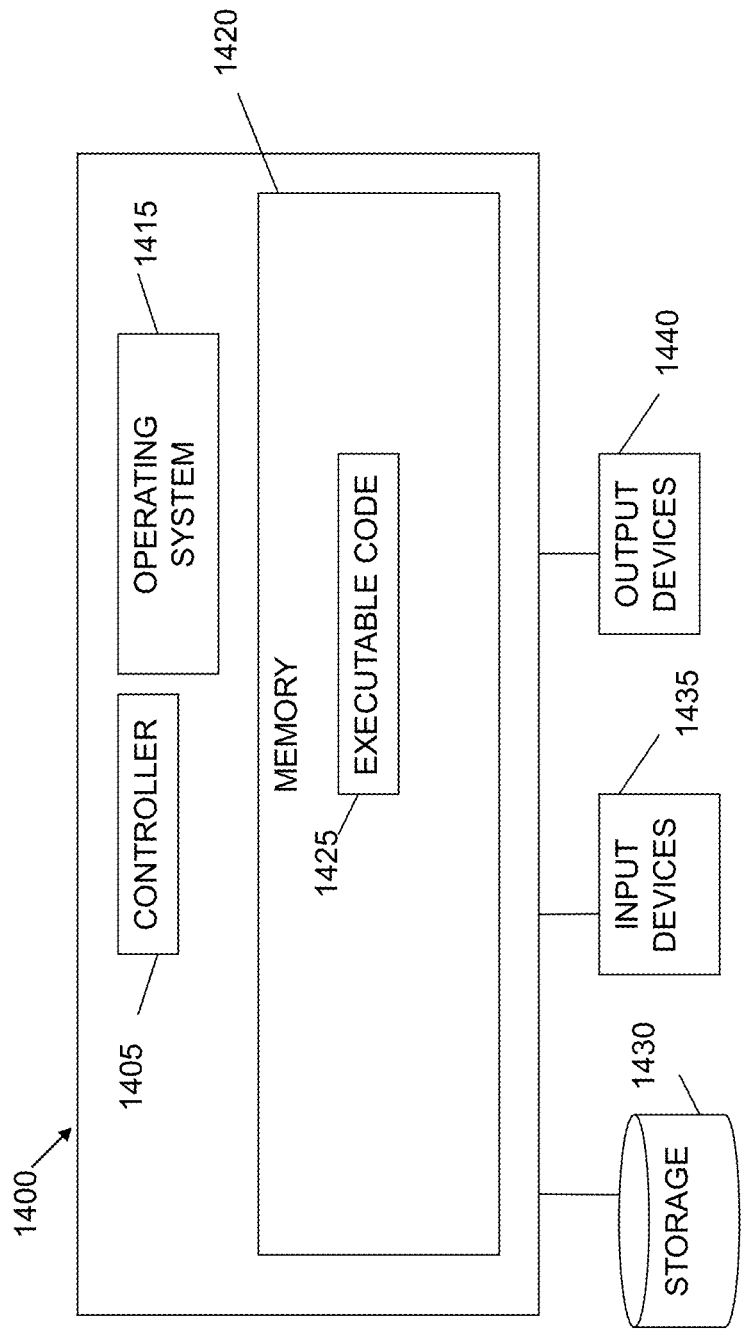
FIG. 10 shows a block diagram of a computing device 1400 which can be used with embodiments of the invention.

It should be noted that although image-to-image location matching is described in the context of an ophthalmic surgical microscope system, the same may be implemented for other surgical microscope systems, such as a brain surgical microscope system, and other surgical applications (e.g. non-microscopic) where guidance may be used in conjunction with live video, such as endoscopic and laparoscopic surgery. In some embodiments, the image-to-image location matching can be used for non-surgical applications, FIG. 10 shows a block diagram of a computing device 1400 which can be used with embodiments of the invention. Computing device 1400 can include a controller or processor 1405 that can be or include, for example, one or more central processing unit processor(s) (CPU), one or more Graphics Processing Unit(s) (GPU or GPGPU), FPGAs, ASICs, combination of processors, video processing units, a chip or any suitable computing or computational device, an operating system 1415, a memory 1420, a storage 1430, input devices 1435 and output devices 1440.

Operating system 1415 can be or can include any code segment designed and/or configured to perform tasks involving coordination, scheduling, arbitration, supervising, controlling or otherwise managing operation of computing device 1400, for example, scheduling execution of programs. Memory 1420 can be or can include, for example, a Random-Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 1420 can be or can include a plurality of, possibly different memory units. Memory 1420 can store for example, instructions to carry out a method (e.g. code 1425), and/or data such as user responses, interruptions, etc.

Executable code 1425 can be any executable code, e.g., an application, a program, a process, task or script. Executable code 1425 can be executed by controller 1405 possibly under control of operating system 1415. For example, executable code 1425 can when executed cause masking of personally identifiable information (PII), according to embodiments of the invention. In some embodiments, more than one computing device 1400 or components of device 1400 can be used for multiple functions described herein. For the various modules and functions described herein, one or more computing devices 1400 or components of computing device 1400 can be used. Devices that include components similar or different to those included in computing device 1400 can be used, and can be connected to a network and used as a system. One or more processor(s) 1405 can be configured to carry out embodiments of the invention by for example executing software or code. Storage 1430 can be or can include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, NN model data, parameters, etc. can be stored in a storage 1430 and can be loaded from storage 1430 into a memory 1420 where it can be processed by controller 1405. In some embodiments, some of the components shown in FIG. 10 can be omitted.

Input devices 1435 can be or can include for example a mouse, a keyboard, a touch screen or pad or any suitable input device. It will be recognized that any suitable number of input devices can be operatively connected to computing device 1400 as shown by block 1435. Output devices 1440 can include one or more displays, speakers and/or any other suitable output devices. It will be recognized that any suitable number of output devices can be operatively connected to computing device 1400 as shown by block 1440. Any applicable input/output (I/O) devices can be connected to computing device 1400, for example, a wired or wireless network interface card (NIC), a modem, printer or facsimile machine, a universal serial bus (USB) device or external hard drive can be included in input devices 1435 and/or output devices 1440.

Embodiments of the invention can include one or more article(s) (e.g., memory 1420 or storage 1430) such as a computer or processor non-transitory readable medium, or a computer or processor non-transitory storage medium, such as for example a memory, a disk drive, or a USB flash memory, encoding, including, or storing instructions, e.g., computer-executable instructions, which, when executed by a processor or controller, carry out methods disclosed herein.

One skilled in the art will realize the invention can be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In the foregoing detailed description, numerous specific details are set forth in order to provide an understanding of the invention. However, it will be understood by those skilled in the art that the invention can be practiced without these specific details. In other instances, well-known methods, procedures, and components, modules, units and/or circuits have not been described in detail so as not to obscure the invention. Some features or elements described with respect to one embodiment can be combined with features or elements described with respect to other embodiments.

Although embodiments of the invention are not limited in this regard, discussions utilizing terms such as, for example, "processing," "computing," "calculating," "determining," "establishing", "analyzing", "checking", or the like, can refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that can store instructions to perform operations and/or processes.

Although embodiments of the invention are not limited in this regard, the terms "plurality" and "a plurality" as used herein can include, for example, "multiple" or "two or more". The terms "plurality" or "a plurality" can be used throughout the specification to describe two or more components, devices, elements, units, parameters, or the like. The term set when used herein can include one or more items. Unless explicitly stated, the method embodiments described herein are not constrained to a particular order or sequence. Additionally, some of the described method embodiments or elements thereof can occur or be performed simultaneously, at the same point in time, or concurrently.

The invention claimed is:

1. A method for determining, for a point in a first image, a matching location in a second image, the first image and the second image are of a patient, the method comprising:
   (a) receiving, via a computing device, the point having a location in the first image;
   (b) receiving, via the computing device, two feature pairs wherein each feature pair comprises one feature location from the first image and a matching feature location from the second image;
   (c) determining, via the computing device, a first triangle with respect to the first image, such that the vertexes of the first triangle are the locations of the two features of the two feature pairs that are from the first image and the location of the point in the first image;
   (d) determining, via the computing device, a second triangle with respect to the second image, such that two of the vertexes of the second triangle are the locations of each of the respective matching features of the two feature pairs that are from the second image, and such that the second triangle has triangle similarity with the first triangle, yielding a location of a third vertex; and
   (e) determining, via the computing device, the matching location in the second image of the point in the first image based on the location of the third vertex, wherein the first image and the second image are selected from at least one of: a preoperative image and an intraoperative image of the patient.

2. The method of claim 1 wherein the two feature pairs are selected from a set of feature pairs.

3. The method of claim 2 wherein the two feature pairs are selected based on distance of the two features of the two feature pairs that are from the first image to the point.

4. The method of claim 1 wherein an order of the vertices in the second triangle proceeding clockwise is the same as the order of the respective matching vertices in the first triangle proceeding clockwise.

5. The method of claim 1 wherein each vertex angle in the second triangle is equal to the vertex angle of its respective matching vertex in the first triangle.

6. The method of claim 1 wherein the images of the patient are images of an eye of the patient.

7. The method of claim 6 wherein the images are of an exterior eye and the feature locations are in the limbus area of the eye in the images.

8. The method of claim 6 wherein the images are of the retina of the eye.

9. The method of claim 1 further comprises repeating the method of claim 1 for each of multiple points, wherein the multiple points are generated from guidance information that is to be overlaid on the second image and wherein the two feature pairs are updated for each of the multiple points.

10. The method of claim 1 further comprising:
repeating steps (b) through (d) for each of a plurality of feature pairs to determine a plurality of corresponding third vertex locations;
calculating an averaged third vertex location; and
determining the matching location in the second image of the point in the first image based on the averaged third vertex location.

11. The method of claim 1, further comprising in step (e), setting the location of the third vertex as the matching location in the second image of the point in the first image.

12. The method of claim 10, further comprising setting the averaged third vertex location as the matching location in the second image of the point in the first image.

* * * * *